United States Patent
Igarashi et al.

(10) Patent No.: US 9,019,360 B2
(45) Date of Patent: Apr. 28, 2015

(54) MICROSCOPE AND A FLUORESCENT OBSERVATION METHOD USING THE SAME

(75) Inventors: Yasunobu Igarashi, Nishitokyo (JP); Takeshi Obara, Sendai (JP); Yuki Deguchi, Ohtsu (JP); Takeshi Suzuki, Maebashi (JP); Koichi Hashimoto, Sendai (JP)

(73) Assignee: Japan Science and Technology Agency, Saitama (JP)

( * ) Notice: Subject to any disclaimer, the term of this patent is extended or adjusted under 35 U.S.C. 154(b) by 936 days.

(21) Appl. No.: 13/061,705

(22) PCT Filed: Jun. 10, 2009

(86) PCT No.: PCT/JP2009/060644
§ 371 (c)(1),
(2), (4) Date: Jun. 21, 2011

(87) PCT Pub. No.: WO2010/029799
PCT Pub. Date: Mar. 18, 2010

(65) Prior Publication Data
US 2011/0242308 A1 Oct. 6, 2011

(30) Foreign Application Priority Data
Sep. 13, 2008 (JP) .................................. 2008-235795

(51) Int. Cl.
*H04N 7/18* (2006.01)
*G02B 21/00* (2006.01)
(Continued)

(52) U.S. Cl.
CPC ........ *G02B 21/0088* (2013.01); *G01N 21/6458* (2013.01); *G02B 21/0076* (2013.01); *G02B 21/16* (2013.01); *G02B 21/26* (2013.01); *G02B 21/34* (2013.01)

(58) Field of Classification Search
CPC ............... G06T 7/0012; G06T 7/0083; G06T 2207/30004; G06T 7/0081; G06T 2207/10064; G06F 19/321; G01N 21/6458; G02B 21/0076; G02B 21/26; G02B 21/365; G02B 21/367; G02B 21/002; H04N 7/18
See application file for complete search history.

(56) References Cited

U.S. PATENT DOCUMENTS 7,253,420 B2    8/2007    Motomura
(Continued)

FOREIGN PATENT DOCUMENTS

CN            101014850 A       8/2007
(Continued)

OTHER PUBLICATIONS

Sitti et al. "Controlled Pushing of Nanoparticles: Modeling and Experiments", IEEE, Jun. 2000.*
(Continued)

*Primary Examiner* — Christopher S Kelley
*Assistant Examiner* — Mohammed Jebari
(74) *Attorney, Agent, or Firm* — Chen Yoshimura LLP

(57) ABSTRACT

A microscope capable of controlling the position and fluorescent recording of an object under observation such as cells is provided with the fluorescent observation method using the microscope. The microscope 1 comprises: a stage 3 on which the object under observation 2 is placed; an illumination light source 4 for the object under observation 2; an excitation light source 5 for exciting fluorescent light F to the object under observation 2; an image information detecting part 16 for detecting the image information formed with the light T generated at the object under observation 2; a fluorescent image information detecting part 17 for detecting the fluorescent image information formed with fluorescent light F; and a control part 20, which determines the fluorescent observation area of the object under observation 2 based on the dynamic model of the object under observation 2 and its image information entered from the image information detecting part 16, and then obtains the image information of the object under observation 2 entered from the image information detecting part 16 and the fluorescent image information entered from the fluorescent image information detecting part 17 at specified interval within the fluorescent observation area.

18 Claims, 14 Drawing Sheets

(51) Int. Cl.
*G01N 21/64* (2006.01)
*G02B 21/16* (2006.01)
*G02B 21/34* (2006.01)
*G02B 21/26* (2006.01)

(56) References Cited

U.S. PATENT DOCUMENTS

| | | | |
|---|---|---|---|
| 7,345,814 | B2 | 3/2008 | Yoneyama et al. |
| 2001/0042816 | A1* | 11/2001 | Fujimoto et al. ............ 250/201.2 |
| 2003/0103662 | A1 | 6/2003 | Finkbeiner |
| 2003/0151742 | A1 | 8/2003 | Silvermintz et al. |
| 2004/0173942 | A1* | 9/2004 | Kobayashi et al. ............ 264/400 |
| 2004/0241832 | A1* | 12/2004 | Muraki et al. ............ 435/287.1 |
| 2005/0068614 | A1 | 3/2005 | Yoneyama et al. |
| 2005/0082494 | A1 | 4/2005 | Motomura |
| 2005/0170332 | A1 | 8/2005 | Shimamoto |
| 2005/0195389 | A1 | 9/2005 | Noy et al. |
| 2005/0219688 | A1* | 10/2005 | Kawano et al. ............ 359/385 |
| 2008/0085550 | A1* | 4/2008 | Werner et al. ............ 435/287.2 |
| 2008/0226126 | A1 | 9/2008 | Ohno |
| 2009/0208072 | A1* | 8/2009 | Seibel et al. ............ 382/128 |

FOREIGN PATENT DOCUMENTS

| | | |
|---|---|---|
| JP | 5-80255 A | 4/1993 |
| JP | 7-253548 A | 10/1995 |
| JP | 7-261097 A | 10/1995 |
| JP | 2000-292422 A | 10/2000 |
| JP | 2005-128086 A | 5/2005 |
| JP | 2005-128493 A | 5/2005 |
| JP | 2005-214924 A | 8/2005 |
| JP | 2006-209698 A | 8/2006 |
| JP | 2006-292420 A | 10/2006 |
| JP | 2007-114130 A | 5/2007 |
| JP | 2008-242014 A | 10/2008 |
| WO | 03/102636 A1 | 12/2003 |

OTHER PUBLICATIONS

Schitter et al. "High performance feedback for fast scanning atomic force microscopes", 2001.*
Oku et al., "Two-dimensional tracking of a motile micro-organism allowing high-resolution observation with various imaging techniques," Review of Scientific Instruments, Feb. 2, 2005, vol. 76, Issue 3, Article 034301, p. 034301-1 to 034301-9.
Oku et al., "High-speed autofocusing of a cell using diffraction patterns," Optics Express, May 1, 2006, vol. 14, Issue 9 (No. 9), p. 3952 to 3960.
Oku et al., "Microscopic visual feedback system," The Transactions of the Institute of Electronics, Information and Communication Engineers D-(II), Jun. 2001, vol. J84-D-II, No. 6, pp. 1-8.
Oku et al., "Structure of Dynamic Focusing Lens with kHz Order Response for High-Speed Vision System," Kogaku (Japanese Journal of Optics), vol. 31, No. 10, pp. 758-764, 2002.
Hashimoto, "Active sensing using microorganisms," SORST Joint Symposium (6), Lecture abstracts, Jan. 30, 2007, pp. 23-26.
Davis, "Intrigue at the Immune Synapse," Nikkei Science, May 2006, pp. 52-60.
Tanimura, "Automated classification of white cells," Medical Imaging Technology, Jan. 1996, vol. 14, No. 1, pp. 14-22.
International Search Report (ISR) issued in PCT/JP2009/060644 (International application) mailed in Aug. 2009 for Examiner consideration.
Written Opinion (PCT/ISA/237) issued in PCT/JP2009/060644 (International application) mailed in Aug. 2009.
European Search Report dated Mar. 21, 2014, in a counterpart European patent application No. 09812947.1.
Rabut et al., "Automatic real-time three-dimensional cell tracking by fluorescence microscopy", Journal of Microscopy, Blackwell Science, Oct. 28, 2004, vol. 216, pp. 131-137, XP002504212, ISSN: 0022-2720, DOI:10.1111/J.0022-2720.2004.01404.X.
Pepperkok et al., "Innovation—High-throughput fluorescence microscopy for systems biology", Jul. 18, 2006, Nature Reviews Molecular Cell Biology, Nature Publising, GB, vol. 7, No. 9, pp. 690-696, XP008097810, ISSN: 1471-0072, DOI: 10.1038/NRM1979.

* cited by examiner

MICROSCOPE AND A FLUORESCENT OBSERVATION METHOD USING THE SAME

TECHNICAL FIELD

The present invention relates to a microscope used for fluorescent observation of body tissues, etc. and a fluorescent observation method for objects to be observed using the same.

BACKGROUND ART

Observation of body tissues and intracellular ions and molecules is an essential technique used in the field of molecular biology. An optical microscope is mainly used to observe body tissues. A laser confocal microscope is used to observe a part of a living cell by irradiating light to that part while moving the position of irradiation.

Major observation techniques of the optical microscope include a fluorescent observation method. In this method, intracellular ions and molecules of body tissues are colored with a fluorescent dye, an excitation light is irradiated to the fluorescent dye, and then the fluorescent light emitted from the excited fluorescent dye is observed.

Since the wavelengths of the fluorescent light and the excitation light are not identical, intracellular molecules can be detected by analyzing the fluorescent light and the molecular concentrations can be measured by analyzing the fluorescent light. The fluorescent observation has the following advantages:
(i) Objects as small as ions and molecules can be observed;
(ii) Only specific ions and molecules can be observed; and
(iii) Since the intensity of the fluorescent light changes depending on the ionic and molecular concentrations, these concentrations can be measured.

However, the fluorescent observation generally has the following disadvantages:
(i) Excitation light having an ultraviolet wavelength band is harmful to cells; and
(ii) When the fluorescent dye is continuously exposed to the excitation light, the fluorescent dye discolors. This means that the intensity of the fluorescent light decreases.

There is a case that the cell may get out of the microscopic field during observing a moving cell by using a fluorescent microscope capable of fluorescent observation and then the observation is interrupted to continue.

To solve this problem, (1) the field of view is enlarged by decreasing the magnification of the objective lens, (2) cellular movement is suppressed mechanically or chemically, or (3) the stage is moved to allow the cell under observation to come to the center of the field of view. However, the method in (1) decreases spatial resolution, whereas the method in (2) may adversely affect the cell under observation.

Regarding the solution in (3), Patent References 1 and 2 disclose optical microscopes equipped with a function of tracking a microscopic cell under observation. These optical microscopes can control the cell position as well as the observation area and make recordings, using transmission light.

Patent References 3 to 5 disclose fluorescent microscopes capable of controlling the cell position as well as the observation area and make recordings, using fluorescent light.

Non-patent References 1 to 5 describe the method of observing a moving paramecium by fastening it within the field of view of a microscope as a relatively large object to be observed.

Immune system cells having a function of protecting human body from bacteria and viruses is valued as primary importance of cells capable of moving freely within a culture solution in the fields of medicine and biology (Non-patent Reference 6).

There are a number of intracellular molecules affecting our immune function, and it is necessary to use a fluorescent observation to detect those molecules and to measure the temporal change of molecular concentrations.

Immune system cells, which are floating in a solution without attaching to the surface of a slide glass, are classified into floating cells. The floating cells within a petri dish change their positions at all times due to the convection of the culture solution, gravity, and interaction with the wall, bottom of the petri dish, solution surface, and other cells. It is considered that one cell tracking method by Oku et al. described in Non-patent Reference 1 may be used to observe floating cells.

PRIOR TECHNICAL REFERENCE

Patent Reference

Patent Reference 1: JP1993-80255 A
Patent Reference 2: JP1995-253548 A
Patent Reference 3: JP1995-261097 A
Patent Reference 4: JP2005-214924 A
Patent Reference 5: JP2006-292420 A
Patent Reference 6: WO2003/102636

Non-Patent Reference

Non-patent Reference 1: H. Oku, N. Ogawa, Ishikawa, K. Hashimoto, "Two-dimensional tracking of a motile microorganism allowing high-resolution observation with various imaging techniques," Review of Scientific Instruments, Vol. 76, No. 3, 2005
Non-patent Reference 2: H. Oku, M. Ishikawa, Theodorus, and K. Hashimoto, "High-speed autofocusing of a cell using diffraction patterns," Optics Express, Vol. 14, No. 9, pp. 3952-3960, 2006
Non-patent Reference 3: H. Oku, I. Ishii, M. Ishikawa, "Microscopic visual feedback system," The Transactions of the Institute of Electronics, Information and Communication Engineers D-(II), Vol. J84-D-II, No. 6, pp. 1-8, 2001
Non-patent Reference 4: H. Oku, M. Ishikawa, "Structure of Dynamic Focusing Lens with kHz Order Response for High-Speed Vision System," Kogaku (Japanese Journal of Optics), Vol. 31, No. 10, pp. 758-764, 2002
Non-patent Reference 5: K. Hashimoto, "Active sensing using microorganisms," SORST Joint Symposium (6), Lecture abstracts, pp. 23-26, Jan. 30, 2007
Non-patent Reference 6: D. M. Davis, "Intrigue at the Immune Synapse," Nikkei Science, pp. 52-60, May 2006
Non-patent Reference 7: Y. Tanimura, "Automated classification of white cells," MEDICAL IMAGING TECHNOLOGY, Vol. 14, No. 1, pp. 14-22, 1996

SUMMARY OF THE INVENTION

Problems to be Solved by the Invention

At present, observers determine fluorescent observation parameters based on empirical rules. In other words, the parameters are not determined by objective evaluation. Consequently, it is difficult for observers to adjust fluorescent observation parameters to cope with the change in position, distribution, type, etc. of the cells under observation.

When the observer should increase excitation light irradiation range or irradiation time excessively, the cells and fluorescent dyes s are adversely affected. Furthermore, as the fluorescent image information obtained increases, it is necessary to require much more time for analyses.

With conventional fluorescent microscopes, the state of activation of ions and molecules within a cell has been continuously observed by automatically controlling the type and intensity of excitation light. And, the interactions between ions and molecules within a cell that occur during an experiment are visualized at once. However, this automatic control may be performed according to preset time schedule, or linked with cell information obtained from fluorescent images.

If fluorescent images only are used for control, the exposure time must be extended to obtain images for control because the intensity of fluorescent light is low. This means that the time for control increases. Consequently, if the maximum cellular migration speed is high, the control tends to be ineffective. The purpose of this type of control is to correct the deviation that occurs when inherently immobile cells are observed for a long time.

Accordingly, to solve the above problem, the object of the present invention is directed to provide a microscope capable of automatically controlling the position of the object under fluorescent observation, observation area, etc. by using transmission light from the object under observation for the control, and a fluorescent observation method using the microscope.

To achieve the above objectives, the present invention provides a microscope comprising: a stage for placing an object under observation; a first light source for irradiating illumination light to the object under observation; a second light source for irradiating excitation light for exciting fluorescent light to the object under observation; an image information detecting part for detecting image information formed by the illumination light generated at the object under observation; a fluorescent image information detecting part for detecting image information formed by the fluorescent light generated by irradiating the excitation light at the object under observation; and a control part for determining the fluorescent observation area of the object under observation based on the dynamic model of the object under observation and the image information of the object under observation input from the image information detecting part and obtaining the image information of the object under observation input from the image information detecting part and the fluorescent image information input from the fluorescent image information detecting part at predetermined intervals within the fluorescent observation area.

The dynamic model is defined as a model intended to forecast spatiotemporal change of the object under observation in a specific feature, among physical or chemical characteristics of the object under observation, by paying attention to a specific feature, combinations of specific features, or combinations of specific features with weight. For example, it is a mathematical model representing the spatiotemporal change of any one of the position, speed, distribution, type, shape, ionic concentration, molecular concentration, etc. of the object under observation, or any combinations of these.

In the above configuration, the control part preferably determines a fluorescent observation area by classic control such as PID control, modern control such as optimum control and sub-optimum control, post-modern control such as H∞ control, sample value control, deadbeat control, and adaptive control, and intelligent control such as neutral network control, fussy control, and genetic algorithm control.

The PID control minimizes the deviation between a target value and actual output according to the control law expressed by any of the term in proportion to the deviation, integral term of the deviation, derivative term of the deviation, or combinations of those.

The optimum control is a control method to create an evaluation function exhibiting the efficiency of fluorescent observation, and the optimum control law is derived by minimizing or maximizing the evaluation function.

The sub-optimum control creates an evaluation function exhibiting the efficiency of fluorescent observation, and by locally minimizing or maximizing that factor, locally optimum control law is derived.

The control preferably determines the central position of the fluorescent observation area according to the dynamic model of the object under observation. The control part is preferably provided with a first light source control for controlling the first light source and a second light source control part for controlling the second light source.

The stage preferably is a three-dimensional one for moving the position of the object under observation.

The fluorescent image information detector part is preferably provided with wavelength selecting means for isolating fluorescent light of one or more wavelengths from each other.

The microscope is preferably provided with a first pinhole installed between the second light source and the object under observation, and a second pinhole is provided between the fluorescent light and the fluorescent image information detecting part. The microscope is preferably provided with a pinhole drive part for moving and/or rotating the first or the second pinhole.

The microscope is preferably provided with an objective lens to be installed between the first light source and the object under observation, and an objective lens drive part. The microscope is also preferably provided with an imaging lens installed between the light from the object under observation and the image information detecting part, and an imaging lens drive part. The microscope is preferably provided with an imaging lens installed between the fluorescent light and the fluorescent image information detecting part and an imaging lens drive part.

The microscope is preferably provided with an environmental control part which houses the object under observation and is filled with an ambient gas. The environmental control part is intended to control the type and the temperature of the ambient gas. As the ambient gas, nitrogen gas, oxygen gas, carbon dioxide, air, and mixture of these gases can be used. The environmental control part is preferably provided with a housing part capable of housing two or more objects to be observed.

The microscope is preferably provided with means for stimulating the object under observation. As stimuli for stimulating the object under observation, electrical, magnetic, mechanical, ultrasonic, thermal, chemical, and optical stimuli can be used. As means for stimulating the object under observation, an electrical and magnetic stimulus control part consisting of electrodes, current, battery, resistor, capacitor, magnet, coil, superconductor, perfect conductor, electrical conductor, semiconductor, insulator, dielectric, piezoelectric, pyroelectric, ferroelectric, ionic conductor, etc. can be used. For example, to apply dynamic stimulus to the object under observation, a dynamic stimulus control part comprising a short needle, probe, actuator, piezoelectric body, centrifuge, weight, spring, etc. can be used. Or to apply ultrasonic stimulus to the object under observation, an ultrasonic stimulus control part such as electrostrictive and magnetostrictive vibrators can be used. Or to apply thermal stimulus to the object under observation, a thermal stimulus control part comprising a heater, cooler, thermal conductor, thermometer, thermograph, etc. can be used. Furthermore, to apply chemical stimulus to the object under observation, a chemical stimulus control part, which varies a concentration of chemical material or varies states on time or in space, such as comprising a pipette, pump, syringe, propeller, screw, and micro fluid device can be used. To apply optical stimulus to the object under observation, an optical stimulus control part comprising a mirror, prism, filter, lamp, laser, and maser can be used.

Needless to say, these stimulus control parts and their components are mutually complementary. For example, with the optical stimulus control part, by applying light to decompose a caged chemical compound, the concentration and the state of chemical substances within and outside cells can be changed spatiotemporally, which allows the optical stimulus part to operate as a chemical stimulus control part. In addition, the optical stimulus control part is capable of warming the fluid to be measured with light, which allows the optical stimulus control part to operate as a thermal stimulus control part.

In another aspect, to achieve the above objectives, the present invention provides a fluorescent observation method comprising: a first step for determining a fluorescent observation area of an object under observation based on an image information of the object under observation and a the dynamic model of the object under observation; and a second step for obtaining a fluorescent image information at predetermined positions within the fluorescent observation area.

In the above configuration, the fluorescent observation area in the first step is preferably determined by classic control such as PID control, modern control such as optimum control and sub-optimum control, post-modern control such as H∞ control, sample value control, deadbeat control, and adaptive control, and intelligent control such as neutral network control, fussy control, and genetic algorithm control.

Between the first and the second steps, the central position of the fluorescent observation area is preferably determined based on either the image information or the dynamic model of the object under observation. In the second step, it is preferable that the image information of the object under observation be obtained. It is desirable that each step be performed for a number of times specified at each position within the fluorescent observation area.

The dynamic model parameters preferably include the position, speed, distribution, type, ionic concentration, molecular concentration, etc., or any combinations of those.

Effects of the Invention

According to the microscope of the present invention, since the fluorescent observation area of the microscope is determined based on the image information and the dynamic model of the object under observation, fluorescent observation can be performed automatically.

According to the fluorescent observation method using the microscope of the present invention, since the position, distribution, type, state, ionic concentration, molecular concentrations, etc. of the object under observation are used as the feedback information to derive the evaluation function and the automatic control law, the fluorescent observation parameters can be adjusted automatically and flexibly to cope with dynamic change of the object under observation.

BEST MODES FOR CARRYING OUT THE INVENTION

Figure 1:
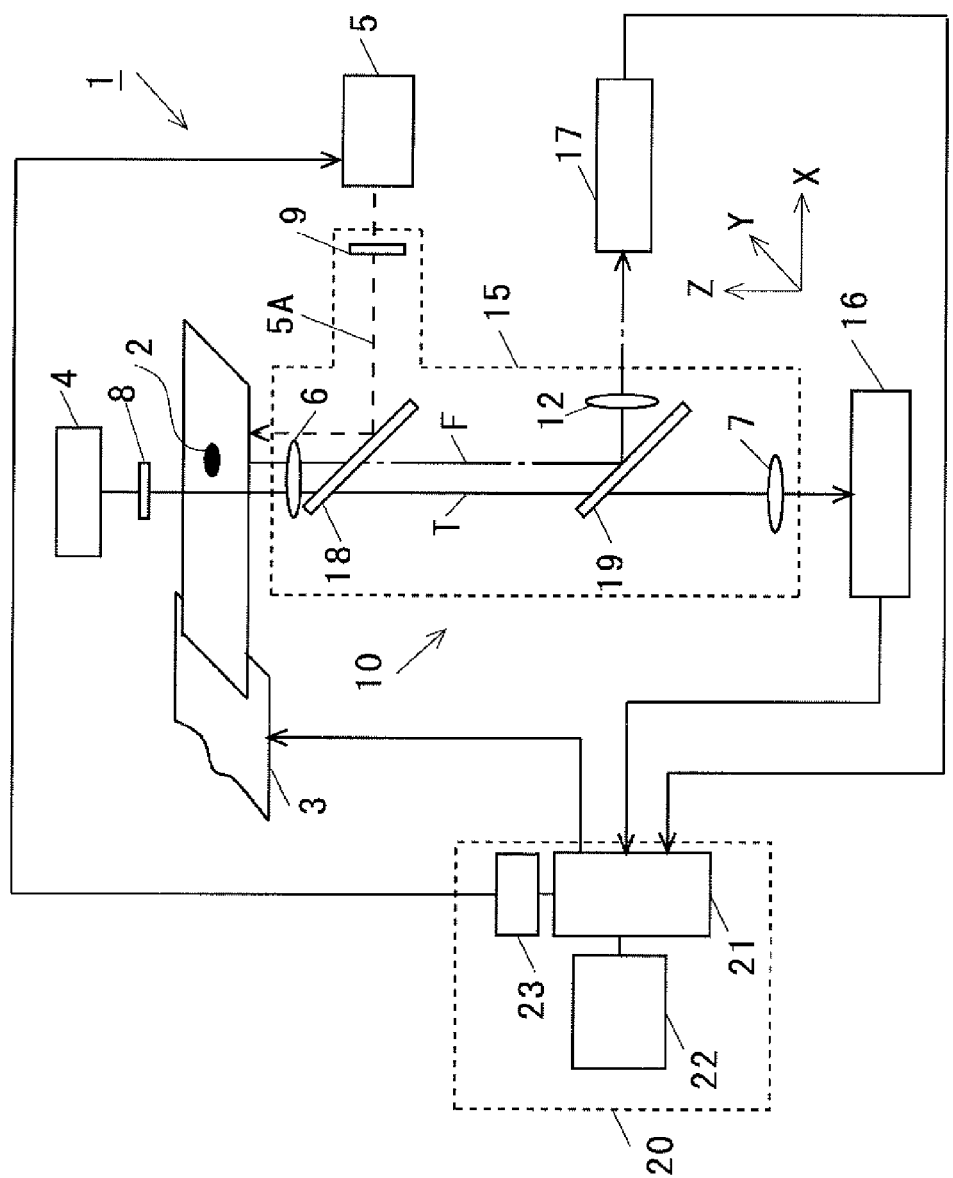
FIG. 1 illustrates a diagram showing the configuration of the microscope in accordance with the Embodiment 1 of the present invention.

The forms of embodiments of the present invention will hereinafter be described in detail by referring to the drawings. The same characters are used to designate the same or corresponding components in each figure.

Embodiment 1

FIG. 1 illustrates a diagram showing the configuration of a microscope 1 in accordance with the Embodiment 1 of the present invention. A microscope 1 in accordance with the Embodiment 1 comprises: a stage 3 for carrying and freely moving an object under observation 2; an optical system 10; and a control part 20 for controlling the position, etc. of the stage 3.

The optical system 10 comprises: an illumination light source 4 for irradiating illumination light to the object under observation 2 to detect an image and a position of the object under observation 2; an excitation light source 5 for irradiating excitation light for exciting fluorescent light generated from the object under observation 2; an optical column part 15 containing optical components for forming a light path of a transmission light T obtained from the object under observation 2 through irradiation from the illumination light source 4, a light path for introducing the excitation light 5A into the object under observation 2, and a light path of the fluorescent light F generated from the object under observation 2; an image information detecting part 16 for detecting the image information formed with the light outgoing from the optical column part 15 and being transmitted through the object under observation 2; and a fluorescent image information detecting part 17 for detecting the fluorescent image information of the object under observation 2 outgoing from the an optical column part 15. The object under observation 2 may be a biological sample cell, etc.

The object under observation 2 is placed on the stage 3 and a position of the object under observation 2 is controlled by the control part 20. The control part 20 will be described later. This stage 3 is a so-called electric stage. This stage 3 can be an XY stage to be drive-controlled on a two-dimensional plane (X-Y plane) on which the object under observation 2 is placed. This stage 3 can be an XYZ stage to be drive-controlled in three-dimensional space. Three-dimensional drive control may be performed with a manipulator (Non-patent Reference 3).

In this case, the positional control with respect to the X and Y axes directions of the observation area may be performed by controlling the irradiation position of the illumination light source 4 or the excitation light source 5. The position control may be performed by adjusting position of a pinhole to be described later. The position control along to Z axis may be performed by adjusting a position of an objective lens, an imaging lens or pinhole to be described later (Patent Reference 6 and Non-patent References 2 and 4).

Any light sources capable of emitting light containing a wavelength to be absorbed or reflected by the object under observation 2 can be used as the illumination light source 4 for transmission light. For example, various lamps such as halogen lamp, light-emitting diode, and various lasers can be used as the illumination light source 4. It is preferable that the wavelength-band, which is the same as that of the excitation light 5A or fluorescent light F of the light output from the illumination light source, may be cut with an optical filter 8, etc. This optical filter 8 serves to prevent the interference of the transmission light T with respect to the excitation light 5A and fluorescent light F. The illumination light irradiated to the object under observation 2 from the illumination light source 4 is detected by the image information detecting part 16 as the transmitted light T or reflected light from the object under observation 2. The image from the object under observation 2 is image information such as so-called bright field image or dark field image.

Any light sources can be used for the excitation light source 5 on condition that it is capable of exciting the object itself under observation 2 or the fluorescent dye contained in the object under observation 2. For example, lamps such as a xenon lamp or mercury lamp and various lasers such as an argon laser can be used as the excitation light 5A. It is desirable that the unnecessary wavelength-band may be cut with an optical filter 9, etc. This optical filter 9 serves to prevent the interference of the excitation light 5A with respect to the transmission light T and the fluorescent light F. The excitation light from the excitation light source 5 may be introduced to the object under observation 2 via a light-guiding tube (not shown).

The optical column part 15 comprises optical components including: a first beam splitters 18; a second beam splitter 19; an objective lens 6; and an imaging lens 7. These optical components serve to form light paths which are generated from the object under observation 2 via the light from the illumination light source 4, excitation light 5A and the fluorescent light F. FIG. 1 is an example of an inverted microscope. In this case, the light generated from the object under observation 2 via the illumination light source 4 can be reflected light instead of transmission light T.

The first and the second beam splitters 18 and 19 may be placed in a port (not shown) installed in the optical column part 15. As beam splitters 18 and 19, dichroic mirrors capable of isolating the wavelength of the illumination light source 4 from that of the fluorescent light F generated from the object under observation 2 can be used. The subsequent description assumes that the beam splitters 18 and 19 are dichroic mirrors.

Since the first dichroic mirror 18 has a function of reflecting the light having a short wavelength and transmitting the light having a long wavelength, the excitation light 5A is reflected and enters into the object under observation 2 as shown at the upper part of the FIG. 1. On the other hand, the transmission light T from the object under observation 2 having a wavelength longer than that of the excitation light 5A is transmitted through the first dichroic mirror 18.

The second dichroic mirror 19 is disposed under the first dichroic mirror 18. The transmission light T from the object under observation 2, which has been transmitted through the first dichroic mirror 18, passes through the second dichroic mirror 19 and the imaging lens 7. The transmission light T is output from the optical column part 15 to the image information detecting part 16. The transmission light T may be made to enter into the image information detecting part 16 without interfering with the excitation light 5A or the fluorescent light F. This may be constructed by placing a filter (not shown) between the imaging lens 7 and the image information detecting part 16.

The fluorescent light F from the object under observation 2 transmitted through the first dichroic mirror 18 is reflected by the second dichroic mirror 19, and it is passed through the imaging lens 12. And the fluorescent light F is then output to the fluorescent image information detecting part 17. The fluorescent light F may be introduced to the fluorescent image information detecting part 17 without interfering with the excitation light 5A or transmitted light T. This may be made by inserting a filter (not shown) between the imaging lens 12 and the fluorescent image information detecting part 17.

The image information detecting part 16 is provided with a detector capable of obtaining image information of the transmission light T or reflected light generated by the illumination light source 4 and by the object under observation 2. The imaging lens 7 is inserted immediately in front of the image information detecting part 16, which detects the transmission light T, along the optical axis of the transmission light T. Image sensors such as CCD and CMOS image sensors can be used as the detector. Furthermore, these image sensors may be cooled with a cooling device using liquid nitrogen or Peltier device to improve the signal-to-noise ratio (S/N), thereby reducing noise. The detector may be equipped with a computer for performing image processing, and an eyepiece for visual observation.

The fluorescent image information detecting part 17 is equipped with a detector capable of obtaining fluorescent images from the object under observation 2. A silver salt camera or an image sensor can be used as the detector depending on intended purposes. As image sensors, CCD and CMOS image sensors can be used as the image information detecting part 16. Furthermore, these image sensors can be cooled with a cooling device using liquid nitrogen or Peltier device to improve the signal-to-noise ratio (S/N), thereby reducing noise. The imaging lens 12 may be installed on the light path of the fluorescent light F and immediately in front of the fluorescent image information detecting part 17 for detecting fluorescent light F. In addition an eyepiece may be provided for a visual observation.

The imaging lens 7 for the image information detecting part 16 and the imaging lens 12 for the fluorescent image information detecting part 17 may differ from each other. For example, the magnification of the imaging lens 7 for the image information detecting part 16 may be decreased. And at the same time, the magnification of the imaging lens 12 for the fluorescent image information detecting part 17 may be increased. In this case, the field of view of the image of the transmission light T obtained by the image information detecting part 16 can be enlarged. At the same time, an enlarged fluorescent image of the object under observation 2 can be obtained in the fluorescent image information detecting part 17.

In FIG. 1, the light paths of the transmission light T, of the excitation light 5A, and of the fluorescent light F are illustrated not to be overlapped only for the explanation. However, these light paths can be overlapped. There may be a case that the central position of the field of view or the focal point of the image information detecting part 16 and the fluorescent image information detecting part 17 may deviate from each other. In this case, the deviation may be measured in advance, and the deviation is used as offset in the positional and observation area control of the object under observation 2. The deviation of the central position of the field of view and focal point can be corrected by using offset.

The image information formed with the transmission light T and reflected light from the object under observation 2 is input into the control part 20 via the image information detecting part 16. The image information is processed by the control part 20. The stage 3 is controlled by the control part 20 based on the results of the image information processing. The control part 20 is equipped with a computer. A personal computer 21 may be used as the computer for the control part 20. A personal computer 21 is equipped with a display device 22 for displaying the images of the object under observation 2. The start and end of imaging, imaging speed, number of pixels of images, number of binning, gain, bit count, etc. of the image information detecting part 16 and the fluorescent image information detecting part 17 are controlled by the personal computer 21.

The image information of the transmission light, which has been transmitted through the object under observation 2 via the optical system 10, is input to the control part 20. Based on this image information, the position of the object under observation 2 on the stage 3 is controlled by the control part 20.

In the microscope 1, the fluorescent observation area of the object under observation 2 is determined by the image information of the object under observation 2 input from the image information detecting part 16 and by the dynamic model of the object under observation 2. In the microscope 1, the image information of the object under observation 2 input from the image information detecting part 16 and the fluorescent image information input from the fluorescent image information detecting part 17 are collected by moving the stage 3 at each predetermined interval of a position within the fluorescent observation area.

In this case, dynamic model parameters include any one of the position, speed, distribution, type, shape, ionic concentration, and molecular concentration (of object under observation 2), or dynamic model parameters include any combinations of these.

Specifically, for the fluorescent observation, the following three steps are controlled by the control part 20 to collect the fluorescent information of the object under observation 2. Steps comprises as follows:

in the first step, the fluorescent observation area of the object under observation 2 is determined based on the image information of the transmission light from the object under observation 2 input from the image information detecting part 16;

in the second step, the central position of the fluorescent observation area is determined according to the dynamic model of the object under observation 2; and in the third step, the fluorescent observation and the bright field observation are performed within the fluorescent observation area at specified interval. The acquisition of fluorescent information of the object under observation 2 can thus be controlled. In this case, the fluorescent observation area can be determined by intellectual control governed by the optimum control law, etc., which will be described later.

(Algorithm of Positional Control)

First, a cellular positional control algorithm i.e. a method of controlling the cell position of the object under observation 2 by (using) the image information of the transmission light from the object under observation 2 used in the first step will be described.

In the image information detecting part 16, transmission light images from the object under observation 2 are collected first, and then image features are extracted from the collected image information. The area containing the target of observation is extracted by binarization of image information. In this case, the image features can be extracted without being bothered by obstacles by employing the self-window method. The self-window method performs extraction in proximity of the area where the target of observation existed immediately before (Non-patent Reference 1).

Specifically, 0th, 1st, and 2nd moments are calculated by binary data mentioned above as image features of transmission light. These image features are read by the personal computer 21 of the control part 20, and a center of gravity and a direction of the object under observation 2 are calculated. The movement of the object under observation 2 can also be predicted by using a Kalman filter, particle filter, etc.

Next, the motor is feedback-controlled so that the target value of the motor rotation angle of the stage 3 is determined to move the center of gravity of the object under observation 2 to the center of the field of view. For example, an XYZ stage can be used as the stage 3. Any one of proportional, integral, and derivative control, or any combinations of these, can be used for this feedback control.

In addition, to observe a specific part of the object under observation 2, or to obtain a three-dimensional image of the object under observation 2, the motor may be feedback controlled so that the target value of the motor rotation angle of the stage 3 intentionally determined to move a specific position deviated from the center of gravity of the object under observation 2 to the center of the field of view.

The image features of transmission light can be extracted by a method other than the self-window method described above. For example, these image features can be extracted from a diffraction image of the object under observation 2 (Non-patent Reference 2).

The displacement information of the XYZ stage 3 is recorded in the personal computer 21 to restructure, namely replay the trajectory of the object under observation 2. Thus, the trajectory of the object under observation 2 can be obtained.

The reason why the transmission light T is used is that the transmission light T has a stable and a high brightness to display the entire image of the object under observation 2. The reflected light from the object under observation 2 by using epi-illumination except transmission light T can also be used. A light source similar to the illumination light source 4 can be used as the light source of the reflected light. In this case, the image from the object under observation 2 is a reflected light image.

If the transmission light T from the illumination light source 4 is irradiated to the object under observation 2 excessively, the temperature of the object under observation 2 may increase. Thus, the control part 20 in the embodiment of the present invention is provided with a function to control the intensity of light and the irradiation time from the illumination light source 4.

(Fluorescent Observation Method)

A fluorescent observation method using the microscope 1 of the present invention will hereinafter be described.

A fluorescent dye is introduced or injected into the object under observation 2. If the object under observation 2 is a biological cell, fluorescent dye such as Indo-1 (AM body, made by DOJINDO LABORATORIES) may be used and applied in an appropriate concentration for a specified period of time. Indo-1 (AM body) does not emit fluorescent light F, but passes through cell membranes.

The Indo-1 (AM body) that has passed through a cell membrane changes into a deacetoxymethyl body i.e. de-AM body by the enzyme i.e. esterase in the cell. In other words, after passing through the cell membrane, Indo-1 (AM body) changes into Indo-1 that emits fluorescent light F but cannot pass through a cell membrane. The fluorescent light F having different wavelength is emitted by Indo-1 depending on whether Indo-1 is combined with $Ca^{2+}$ ions or dissociated from $Ca^{2+}$ ions.

The amount of Indo-1 in a state combined with or dissociated from $Ca^{2+}$ ions changes depending on the concentrations of $Ca^{2+}$. When concentration of $Ca^{2+}$ is increased, the fluorescent light F from Indo-1 in combined state increases and in contrast with this, the fluorescent light F from Indo-1 in dissociated state decreases. By virtue of these characteristics, the concentration of $Ca^{2+}$ concentration can be obtained by comparing the intensity of the fluorescent light F in each wavelength. Specifically, when a microscope 40, which will be described later, is used, the concentration of $Ca^{2+}$ can be obtained by dividing 2-wavelength fluorescent observation images by each wavelength and substituting the fluorescent light intensity ratio calculated for each pixel into a calibration curve created in advance.

Fluorescent dyes s not only for $Ca^{2+}$ ions but also for other ions and molecules can be used by replacing the filter 9 and dichroic mirrors 18, 19, and 26 in the microscope 1.

(Algorithm for Control of Fluorescent Observation Area)

The control for reducing the number of times of fluorescent observation and increasing the number of cells that can be subjected to fluorescent observation will hereinafter be described by referring to the microscope 1.

As for fluorescent observation, the positional change in the Z-axis direction of the stage 3, namely, the temporal change of the position of the imaging lens 7, more specifically, the temporal change of the width of the fluorescent observation area is controlled.

Figure 2:
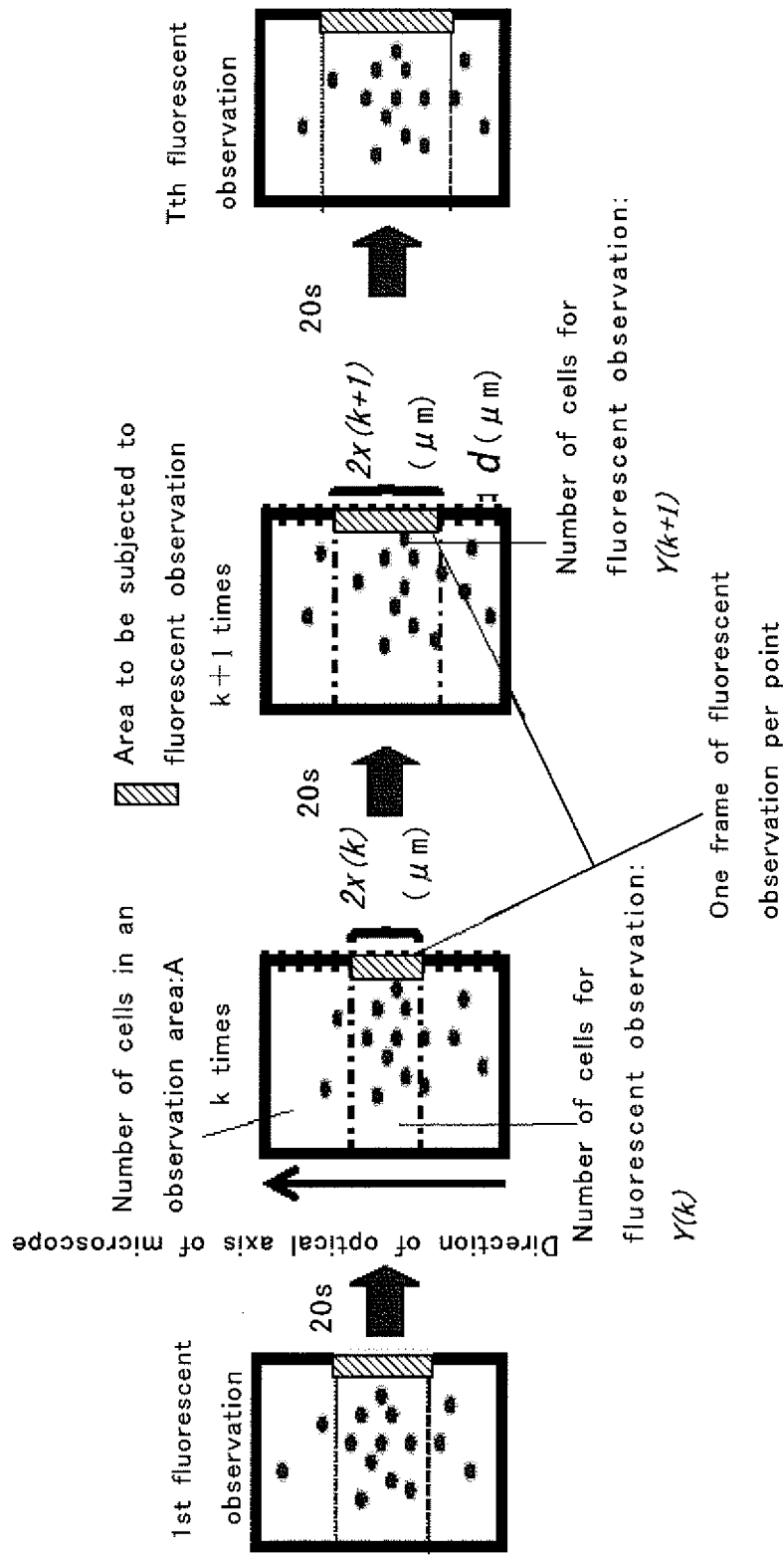
FIG. 2 illustrates a fluorescent observation area model.

The first step of the fluorescent observation is to determine an area to be subjected to fluorescent observation. FIG. 2 illustrates a fluorescent observation area model. The section marked with diagonal lines is the area to be subjected to fluorescent observation. This observation area is divided into equal parts. The division width d (d>0) is determined depending on the target of observation. Fluorescent observation is then performed at each point within the observation area. After waiting for several tens of seconds, the observation area is reset to a new area, and fluorescent observation is performed again. The observation is thus repeated for the number of times of T (T>0).

When the excitation light 5A is irradiated for the single fluorescent observation, the total time period eN(k) is given by the time e (>0), for irradiating excitation light 5A for single fluorescent observation, multiplied by the number of points for observation of N(k) (k>0). Although e can be made variable, it is assumed to be non-variable here for simplification. The width of the area for the k∈{0, 1, . . . , T−1}th fluorescent observation, 2x(k), is given by the following formula (1).

[Formula 1]

$$2x(k) = N(k)d \quad (1)$$

When the fluorescent observation time is transferring from the k th trial to (k+1) th fluorescent light F, x(k) is to updated to x(k+1).

As an evaluation function of fluorescent observation, J(T), which is given by the following formula (2), is used.

[Formula 2]

$$J(T) = \sum_{k=0}^{T} [qeN^2(k) - ry^2(k)] \quad (2)$$

where q (>0) and r (>0) are weights for the fluorescent observation time and for the number of cells observed respectively. y(k) is the number of cells observed by fluorescent observation within the fluorescent observation width 2x(k). In the formula (2), the value of right side of the formula (2) is decreased when the smaller the number of pieces for fluorescent observation, N(k), and the value of right side of the formula (2) is decreased when the larger the number of cells y(k) subjected to fluorescent observation. On the other hand, with the decrease in N(k), y(k) also decreases.

From the above, the problem is regarded as the one to find the fluorescent observation parameter N(k) for minimizing the evaluation function J(T). Since N(k) and x(k) have the relation expressed by the formula (1), the optimum control law of x(k) will be solved as described below.

The value x(k) at time k is updated according to the following formula (3):

[Formula 3]

$$x(k+1) = x(k) + u(k) \quad (3)$$

where x(k) is a positive value. The controlled variable u(k) is obtained by feedback of the observation value y(k) of the number of cells. The formula (3) indicates that x(k+1) of the next time is found by adding the controlled variable u(k) to x(k) of the current time.

From the above, the problem of finding x(k) leads to finding the optimum controlled variable, $U^*(T-1) = [u^*(0), u^*(1), \ldots, u^*(T-1)]$, which is regarded as a problem of finding the optimum output feedback law of control theory. Consequently, it is the problem that the optimum control law $U^*(T-1) = [u^*(0), u^*(1), \ldots, u^*(T-1)]$ that satisfies the optimum control law $U^*(T-1)$ of the following formula (5) is to be found.

[Formula 4]

$$U*(T-1) = \arg\min_{U(T-1)} J(T) \quad (4)$$

In finding the controlled variable u(k), attention should be paid to the movement of the cell 2 along the direction of the optical axis of the microscope 1. This is because that there may be a case in which the cell 2 is escaped from the fluorescent observation area by depending on the movement of the cell 2 in the direction of the optical axis of the microscope 1. Thus, a model for forecasting the movement of the cell 2 along the direction of the optical axis of the microscope 1 is used. And the relation between the width of the fluorescent observation area 2x(k) and the number of cells y(k) existing in this area is to be found.

The total number of cells is defined as M. The number for identifying the cell 2 is defined as i, and i falls within the range, i∈{1, 2, ..., M}. The position $z_i(k)$ (>0) of the cell 2 in the direction of the optical axis of the microscope 1 is expressed by the following formula (5):

[Formula 5]

$$z_i(k+1) = z_i(k) + v_0 + \omega_i(k) \quad (5)$$

where $v_0$ is a constant representing the ensemble average of the velocity of the cell 2. $\omega_i(k)$ is white noise included in the term of the movement of the cell 2. The characteristics of $\omega_i(k)$ are given: Average $E[\omega_i(k)] = 0$, and its variance is assumed to be given by the following formula (6):

[Formula 6]

$$E[\omega_i(k)\omega_j^T(\tau)] = W_i \delta_{k\tau} \delta_{ij} \quad (6)$$

where $\delta_{k\tau}$ and $\delta_{ij}$ are Kronecker deltas. T represents inversion.

The initial position $z_i(0)$ is a random variable with the average given by the following formula (7), and known variance is given by the following formula (8). $v_0$ and $\omega_i(k)$ are independent from each other.

[Formula 7]

$$E[z_i(0)] = \bar{z}_i(0) \quad (7)$$

[Formula 8]

$$E[(z_i(0) - \bar{z}_i(0))^2] = P_i(0) \quad (8)$$

From the above formula (5), the time updating formula of the variance $P_i(k)$ of $z_i(k)$ is given by the following formula (9):

[Formula 9]

$$P_i(k+1) = P_i(k) + W_i \quad (9)$$

By providing the distribution of the cell 2 as a dynamic model of the cell 2, the average and the variance of the cell position at each time can be found. The ensemble average of the cell position, $\bar{z}(k)$, is given by the following formula (10). The ensemble average of the variance of the cell position P(k) is given by the following formula (11):

[Formula 10]

$$\bar{z}(k) = \frac{1}{M} \sum_{i=1}^{M} z_i(k) \quad (10)$$

[Formula 11]

$$P(k) = \frac{1}{M} \sum_{i=1}^{M} P_i(k) \quad (11)$$

When there is sufficient number of cells, the distribution of the cells 2 can be regarded as normal distribution according to the central limit theorem. Consequently, the distribution of the cell position 2 in the direction of the optical axis of the microscope 1 at k is given by the probability density function h(z(k)) of the following formula (12):

[Formula 12]

$$h(z(k)) = \frac{1}{\sqrt{2\pi P(k)}} \exp\left[-\frac{(z(k) - \bar{z}(k))^2}{2P(k)}\right] \quad (12)$$

In this case, from the above formulae (9) to (12), the update of time of P(k) and $\bar{z}(k)$ are given by the following formulae (13) and (14) respectively. The center of the fluorescent observation area is controlled to coincide with $\bar{z}(k+1)$ of the formula (14).

[Formula 13]

$$P(k+1) = P(k) + \frac{1}{M} \sum_{i=1}^{M} W_i \quad (13)$$

[Formula 14]

$$\bar{z}(k+1) = \bar{z}(k) + v_0 \quad (14)$$

The distribution of the number of cells f(k, n(k)) in the direction of the optical axis of the microscope 1 at k is defined as M times the probability density function h(n(k)) as shown by the following formula (15). The reason for this is that if h(n(k)), which is normal distribution, is integrated with respect to n(k) for the section from to $-\infty$ to $+\infty$, 1 is obtained, but the value of integral of f(k, n(k)) for the same section becomes M from its definition.

[Formula 15]

$$f(k, n(k)) = Mh(n(k)) \quad (15)$$

The number of cells y(k) existing within the width 2x(k) of the observation area in the direction of the optical axis of the microscope 1 is given by the following formula (16):

[Formula 16]

$$y(k) = g(k, x(k)) \quad (16)$$
$$= \int_{\bar{z}(k)-x(k)}^{\bar{z}(k)+x(k)} f(k, n(k)) \, dn(k)$$
$$= M\sqrt{1 - \exp\left[-\frac{x^2(k)}{2P(k)}\right]}$$

If linear approximation with respect to x(k) is performed with the above formula (16) about y(k), the following formula (17) is obtained:

[Formula 17]

$$y(k) = c(k)x(k) + s(k) \quad (17)$$

where c(k) is a coefficient multiplied to x(k) and c(k) is given by the following formula (18):

[Formula 18]

$$c(k) = \frac{\partial g}{\partial x}\bigg|_{x=x(k-1)} \quad (18)$$
$$= \frac{1}{2} M \frac{x(k-1) \exp\left[-\frac{x^2(k-1)}{2P(k)}\right]}{P(k)\sqrt{1 - \exp\left[-\frac{x^2(k-1)}{2P(k)}\right]}}$$

From the formula (18), it is clear that c(k)>0 holds when x(k−1)>0. This means that with respect to the observation width, the number of cells existing within the observation width increases monotonically, which is physically valid.

The term s(k), which does not contain x(k), is given by the following formula (19):

[Formula 19]

$$s(k)=g(k,x(k-1))-c(k)x(k-1) \quad (19)$$

Next, how to derive the optimum controlled variable will be described.

By substituting the formulae (1) and (17) into the formula (2) and organizing the evaluation function J(T), J(T) is found by the following formula (20):

[Formula 20]

$$J(T) = \sum_{k=0}^{T} [q_2(k)x^2(k) + \alpha(k)x(k) + \beta(k)] \quad (20)$$

where $q_2(k)$, $\alpha(k)$, and $\beta(k)$ are given by the following formula (21):

[Formula 21]

$$q_2(k)=4qe/d^2-rc^2(k),$$

$$\alpha(k)=-2rc(k)s(k),$$

$$\beta(k)=-rs^2(k) \quad (21)$$

The sum total $\bar{J}(1)$ of the evaluation function in the observation having the evaluation section from 1 to the number of times of T is defined by the following formula (22):

[Formula 22]

$$\bar{J}(l) = \sum_{k=l}^{T} [q_2(k)x^2(k) + \alpha(k)x(k) + \beta(k)] \quad (22)$$

where l falls within the range l∈{1, 2, . . . , T−1}.

By using the principle of mathematical induction, $\bar{J}(m)$ at l=m is found by the following formula (23):

[Formula 23]

$$\bar{J}(m) = \sum_{k=m+1}^{T} \left\{ q_2(k)\left[u(k-1)+x(k-1)+\frac{\alpha(k)}{2q_2(k)}\right]^2 \right\} + \quad (23)$$

$$q_2(m)x^2(m) + \alpha(m)x(m) + \sum_{k=m}^{T} \beta(k) - \sum_{k=m+1}^{T} \frac{\alpha^2(k)}{4q_2(k)}$$

By applying the principle of optimality to the formula (23), the optimum controlled variable u*(k) is given by the following formula (24):

[Formula 24]

$$u^*(k) = -x(k) - \frac{\alpha(k+1)}{2q_2(k+1)} \quad (24)$$

Furthermore, if the optimum controlled variable u*(k) of the formula (24) is rewritten using the expression (17), the optimum controlled variable u*(k) is given by the following formula (25):

[Formula 25]

$$u^*(k) = -c^{-1}(k)y(k) - \frac{\alpha(k+1)}{2q_2(k+1)} + c^{-1}(k)s(k) \quad (25)$$

The above formula (25) indicates that the optimum controlled variable u*(k) is given by feedback of the observation value y(k) of the number of cells.

(Image Processing)

Image processing for measuring the number of cells, etc. required to obtain the optimum controlled variable will hereinafter be described.

The ensemble average $v_0$ of velocity of the cell 2 in the direction of the optical axis of the microscope 1 and the temporal change $W_i$ of the variance of the cell position are required to identify the dynamic model of the cell 2. If the object under observation 2 is a stationary body, the ensemble average $v_0$ of the transfer speed and the temporal change $W_i$ of the variance of the position can be regarded as 0 i.e. zero.

In measurement of the number of cells, there may be a case in which the cell 2 existing deviated from the focal point is counted. In this case, the measurement is made assuming that the cell 2 exists in a position where the cell 2 actually does not exist. This results as a measurement error. Thus, a method of estimating the cell position is essential. The Becke's line method, etc. can be used to estimate the cell position.

When the position of the cell 2 falls within the focal distance of the objective lens 6, bright stripes appear inside the cell 2 and black ones appear on the periphery of the cell 2. When the position of the cell 2 falls far from the focal distance of the objective lens 6, bright stripes appear outside of the cell 2 and black ones appear inside of the cell 2. These stripes are called as Becke's lines. This line appears due to significant change in diffraction of light between both sides of the focal plane when observing the cell 2. By using the Becke's lines for image processing, the cell position 2 in the direction of the optical axis of the microscope 1 can be estimated (Non-patent Reference 2).

According to the above image processing procedure, since the cell position is estimated using the Becke's method, the cellular count error that may occur when the cell 2 exists deviated from the focal point can be minimized.

The process of transmission light images can be performed by following steps as shown below:

(i) The observation area of the test solution in which the cell 2 is floating shall be in the direction of the optical axis of the microscope 1. The object under observation 2 is taken an image by a camera, etc. installed in the image information detecting part 16. The image obtained is named as observation image 1. The observation image 1 obtained is a bright field image;

(ii) Another image is taken at a place that is closer to the objective lens 6 by the predetermined distance than the observation image obtained in step (i), and this image is named as observation image 2. The predetermined distance may be on the order of 1 μm, for example;

(iii) The difference between the observation image 1 and observation image 2 is obtained;

(iv) The obtained difference on the image is binarized;

(v) Expansion processing is performed using a circular mask with pixels having the diameter of predetermined value, and separate pixels of the same cell 2 are unified;
(vi) Reduced processing is performed using the circular mask described in (v) with the above pixels, and small noise other than the cell 2 is removed;
(vii) 8 adjacent pixels are coupled, labeled, and the number of cells is counted; and
(viii) Filtering is performed depending on the size of the cell 2 labeled. Specifically, the cell whose size is too large is counted as two cells to compensate for the case in which separate cells 2 are regarded as one cell in step (v). The cell whose size is too small is regarded as noise to cope with the case in which existence of substances other than the cell 2 cannot be eliminated.

The above image processing can be performed by using the image information detecting part 16 and the control part 20 and the stage 3 of the microscope 1, following steps from (1) to (7) as shown below.
 (1) An instruction is provided by the personal computer 21.
 (2) The voltage is output by the D/A board receiving the instruction from the personal computer 21.
 (3) The stage 3 is moved.
 (4) The image obtained through the objective lens 6 is taken by a camera.
 (5) The image obtained is sent to the personal computer 21.
 (6) The image processing is performed by the personal computer 21.
 (7) Based on the information having finished image processing, an instruction to the D/A board is provided by the personal computer 21.

The numbers of cell of each image is measured by the image processing. This cell count corresponds to the number of cells at each observation point in the observation area. Accordingly, the cell distribution within the observation area can be obtained. Using the number of cells at each observation point, $\bar{z}(k)$ is calculated, and the amount of change in $\bar{z}(k)$ with respect to the temporal change can be found as the ensemble average $v_0$ of the cell transfer speed.

Furthermore, the temporal change of the variance of cell position $W_i$ can also be obtained.

Next, the fluorescent observation combining the optimum control law for fluorescent observation described above and the image processing for measurement of the number of cells required to apply the optimum control law will hereinafter be described.

Figure 3:
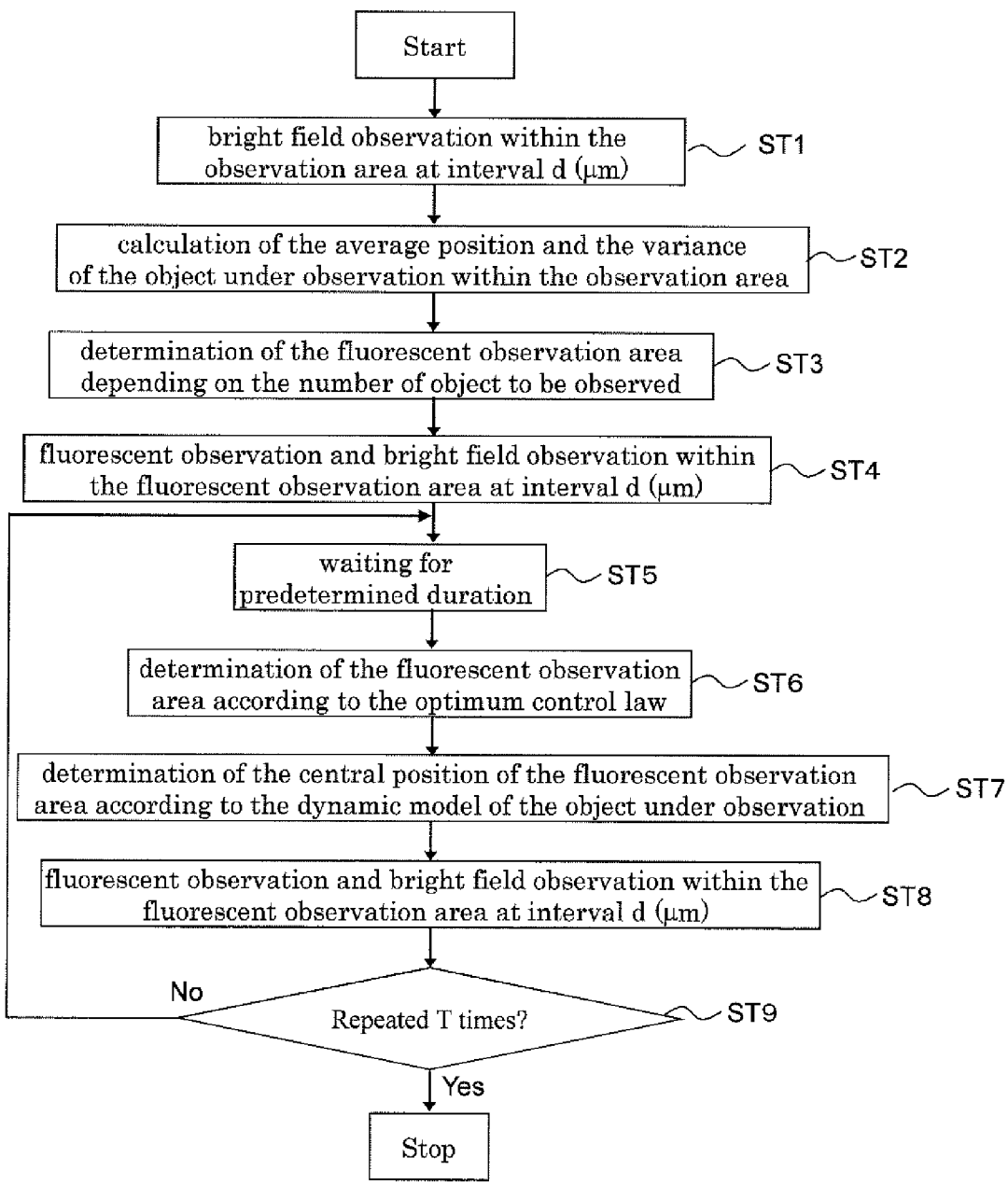
FIG. 3 is a flow chart illustrating the fluorescent observation procedure using the microscope in accordance with the Embodiment 1.

FIG. 3 is a flow chart illustrating the fluorescent observation steps using the microscope 1 in accordance with the Embodiment 1 of the present invention.

First, in step ST1, bright field observation of the object under observation 2 is performed within the observation area and at predetermined interval, namely interval d (μm) (hereinafter referred to as interval d). The object under observation 2 is a T cell, which is a kind of immune system cells, for example.

In step ST2, the average position and the variance of the object under observation 2 within the observation area are calculated.

In step ST3, the fluorescent observation area is determined depending on the number of objects to be observed 2.

In step ST4, the fluorescent observation and bright view observation within the fluorescent observation area are performed at interval d. To increase the information on transmission light images, the observation interval of the bright view observation may be made smaller, or its observation area may be enlarged, with respect to the fluorescent observation.

In step ST5 is a standby period for predetermined duration, for example 20 seconds. To increase the image information of the transmission light for control, the standby time of the bright field observation may be made shorter compared with that of fluorescent observation.

In step ST6, the fluorescent observation area is then determined by the optimum control law.

In step ST7, the central position of the fluorescent observation area is determined based on the dynamic model of the object under observation 2.

In step ST8, the fluorescent observation within the fluorescent observation area and bright field observation are performed at an interval d. The interval d may be 300 μm, for example. To increase the information of transmission light images, the observation interval of the bright field observation may be narrowed, or its observation area may be enlarged, compared with those of fluorescent observations.

In step ST9, whether the fluorescent observation is to be terminated or not is judged. If it is judged that fluorescent observation has not been repeated for predetermined number of times such as number of times of T for example in step ST9, the fluorescent observation in steps from ST5 to ST8 is repeated.

If it is judged in step ST9 that the measurement of the object under observation 2 in steps from ST5 to ST8 has been conducted for the number of times of T, the fluorescent observation is terminated. The fluorescent observation of the object under observation 2 can thus be conducted according to the optimum control law.

In the first trial for k=0th time, the entire observation area is observed at interval d. In trials for k=1st and subsequent ones, the width of fluorescent observation area 2x(k) is observed. x(k) is determined according to the optimum controlled variable U*(k).

The center of the fluorescent observation area, $\bar{z}(k)$, is updated using the dynamic model parameter $v_0$ of the cell 2 found by following the transmission light image processing procedures described in step (i) to step (viii) described above. A bright field observation image of a gray scale of predetermined bit, 8 bits for example, is taken at the central $\bar{z}(k)$ and width x(k) with a camera installed in the image information detecting part 16. This gray scale image is subjected to image processing, and x(k+1) of the (k+1)th trial is determined. At the same time, the fluorescent observation image is taken by a camera for fluorescent observation installed in the fluorescent image information detecting part 17.

According to the microscope 1, the fluorescent observation parameters, which have conventionally been found manually by observers prior to fluorescent observation, can be set automatically. Thus, this automation reduces the workload on observers.

Further, the control of the fluorescent observation and the recording of the fluorescent images can be processed further by the control part 20. As shown in FIG. 1, the control part 20 may further comprise an excitation light source control part 23 as a second light source control part for controlling the excitation light source 5. The excitation light source control part 23 is equipped with a function of controlling the on and off and ON time of the excitation light 5A according to the image data of the object under observation 2 formed with transmission light T. Furthermore, the excitation light source control part 23 may be equipped with a function of selecting the wavelength and intensity of the excitation light 5A for irradiation.

To perform recording and image processing of fluorescent images, the detected output from the fluorescent image information detecting part 17 is input into the control part 20.

Furthermore, according to the microscope 1, the information of the object under observation 2 obtained from the transmission light images has more light quantity compared with the fluorescent light F from the object under observation 2, and is recorded at high speed compared with the fluorescent light F from the object under observation 2. Thus, the space and time accuracy of result of analysis of the fluorescent image can be increased by the transmission light images obtained together with the fluorescent light F.

With the microscope 1, the fluorescent images of the fluorescent image information detecting part 17 can be recorded in conjunction with the cell information obtained from transmission light images such as positions. In other words, it is only necessary to record fluorescent images while the fluorescent light F is irradiated only. Consequently, when the object under observation 2 is not within the field of view of the microscope 1, it is not necessary to record the fluorescent image. Therefore, it reduces the operating time or the capacity of the storage device for fluorescent image recording, thus leading to the efficient use of the personal computer 21. Since it is not necessary to record unavailing fluorescent image, the time required for analyses of fluorescent images can be reduced significantly.

Further, the control of fluorescent observation using transmission light images according to the present invention can be generalized as a problem of scheduling. Consequently, in addition to the optimum control law described above, classic control such as PID control, modern control such as sub-optimum control, post-modern control such as H∞ control, sample value control, deadbeat control, and adaptive control, and intelligent control such as neutral network control, fussy control, and genetic algorithm control etc. may be used for the control of the fluorescent observation.

Furthermore, the microscope 1 may have various forms of Embodiments as shown below.

Embodiment 2

Figure 4:
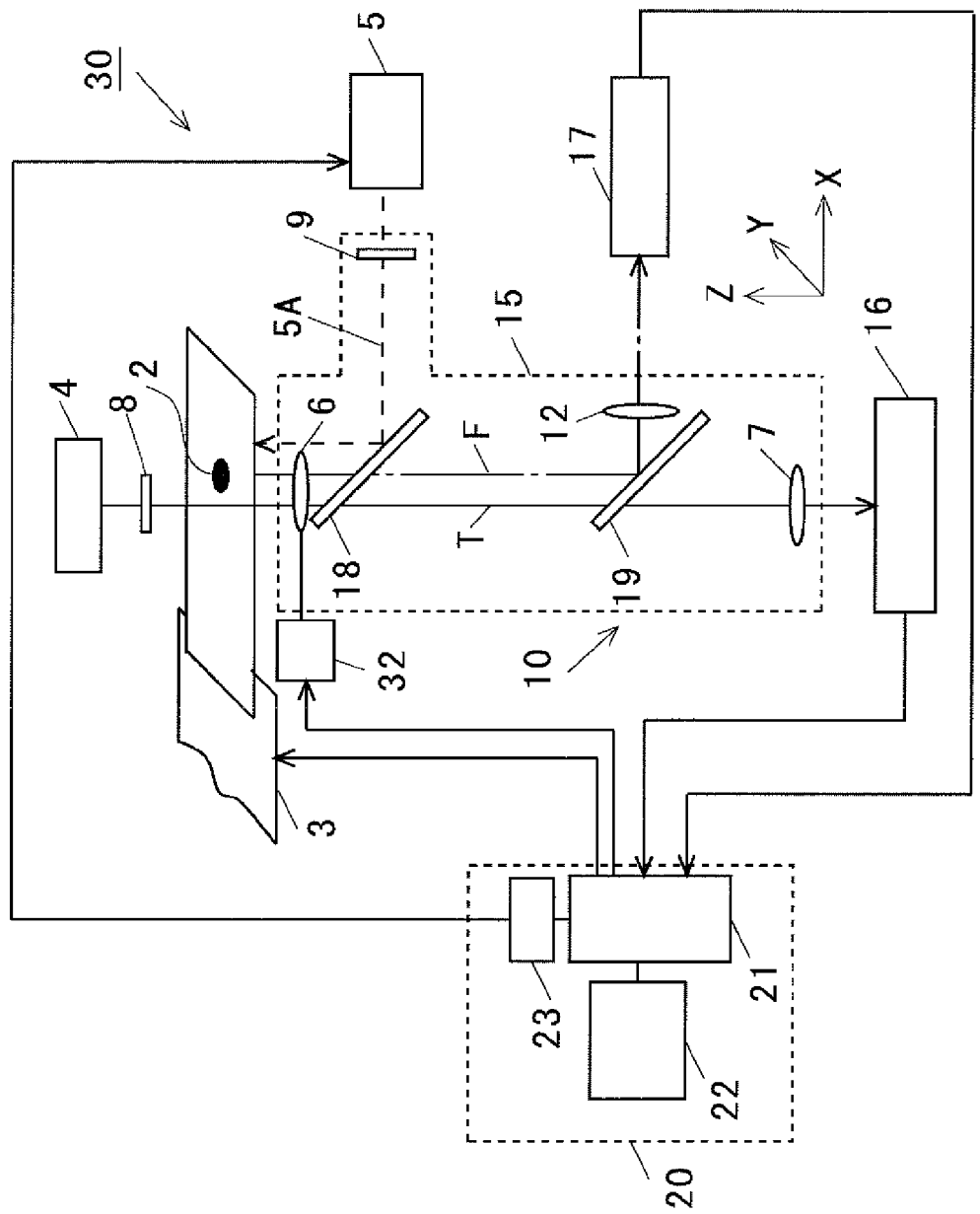
FIG. 4 illustrates a diagram showing the configuration of the microscope in accordance with the Embodiment 2.

FIG. 4 illustrates a diagram showing the configuration of the microscope 30 in accordance with the Embodiment 2 of the present invention. The configuration of the microscope 30 is the same as that of the microscope 1 except that an objective lens drive part 32 is provided to move the objective lens 6 in the direction of the optical axis of the transmission light T, namely in the direction of Z-axis. The objective lens drive part 32 is controlled by the control part 20. The objective lens drive part 32 can be configured using a driving part such as piezoelectric element. Description of the rest of the configuration will be omitted because it is the same as that of the microscope 1.

Embodiment 3

Figure 5:
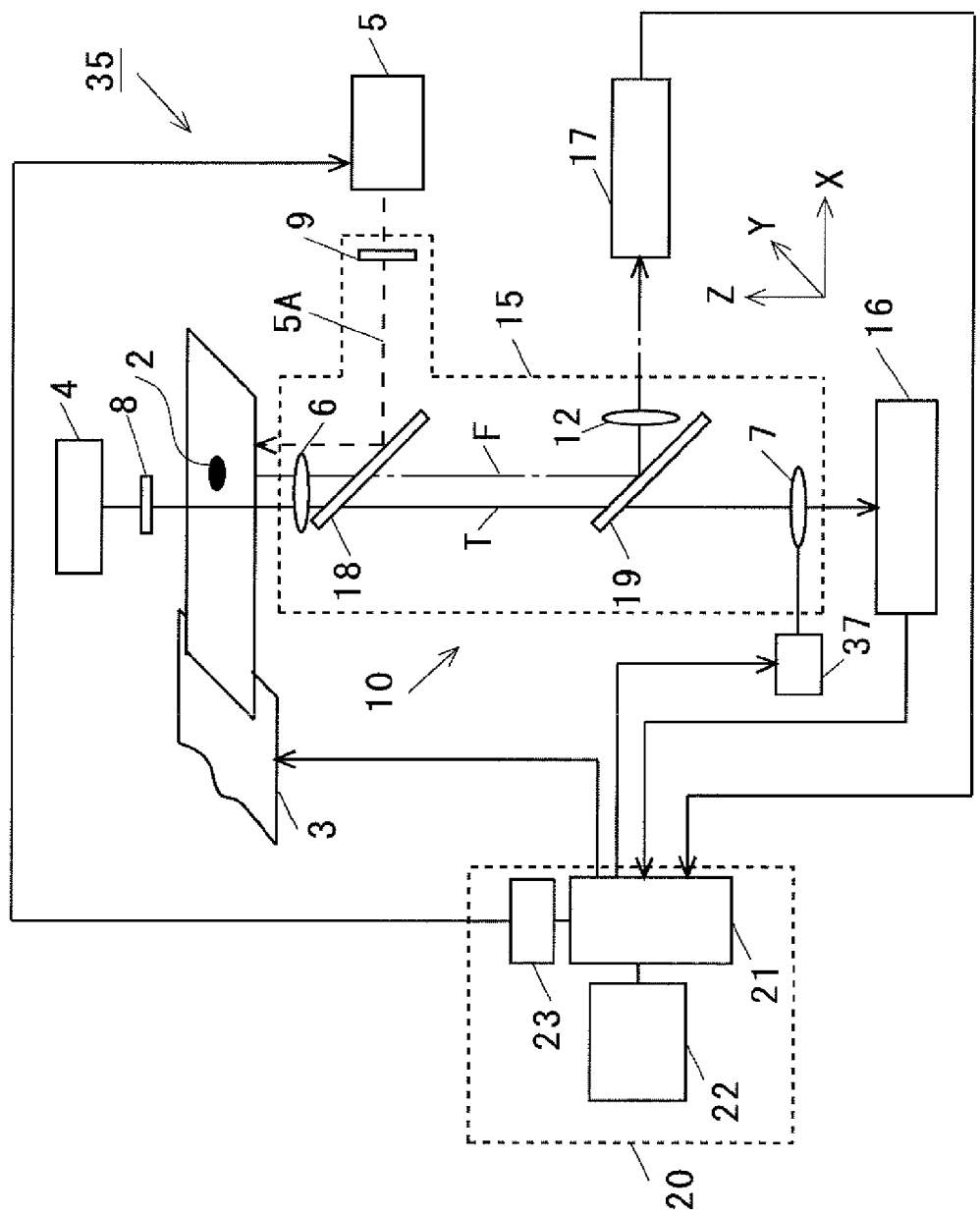
FIG. 5 illustrates a diagram showing the configuration of the microscope in accordance with the Embodiment 3.

FIG. 5 illustrates a diagram showing the configuration of the microscope 35 in accordance with the Embodiment 3 of implementation of the present invention.

The configuration of the microscope 35 is the same as that of the microscope 1 except that a transmission light imaging lens drive part 37 is provided to move the imaging lens 7 on the side of the image information detecting part 16 in the direction of the optical axis (direction of Z-axis). The imaging lens drive part 37 is controlled by the control part 20. The imaging lens drive part 37 may be configured using a drive part such as piezoelectric element. Description of the rest of the configuration will be omitted because it is the same as that of the microscope 1.

Embodiment 4

Figure 6:
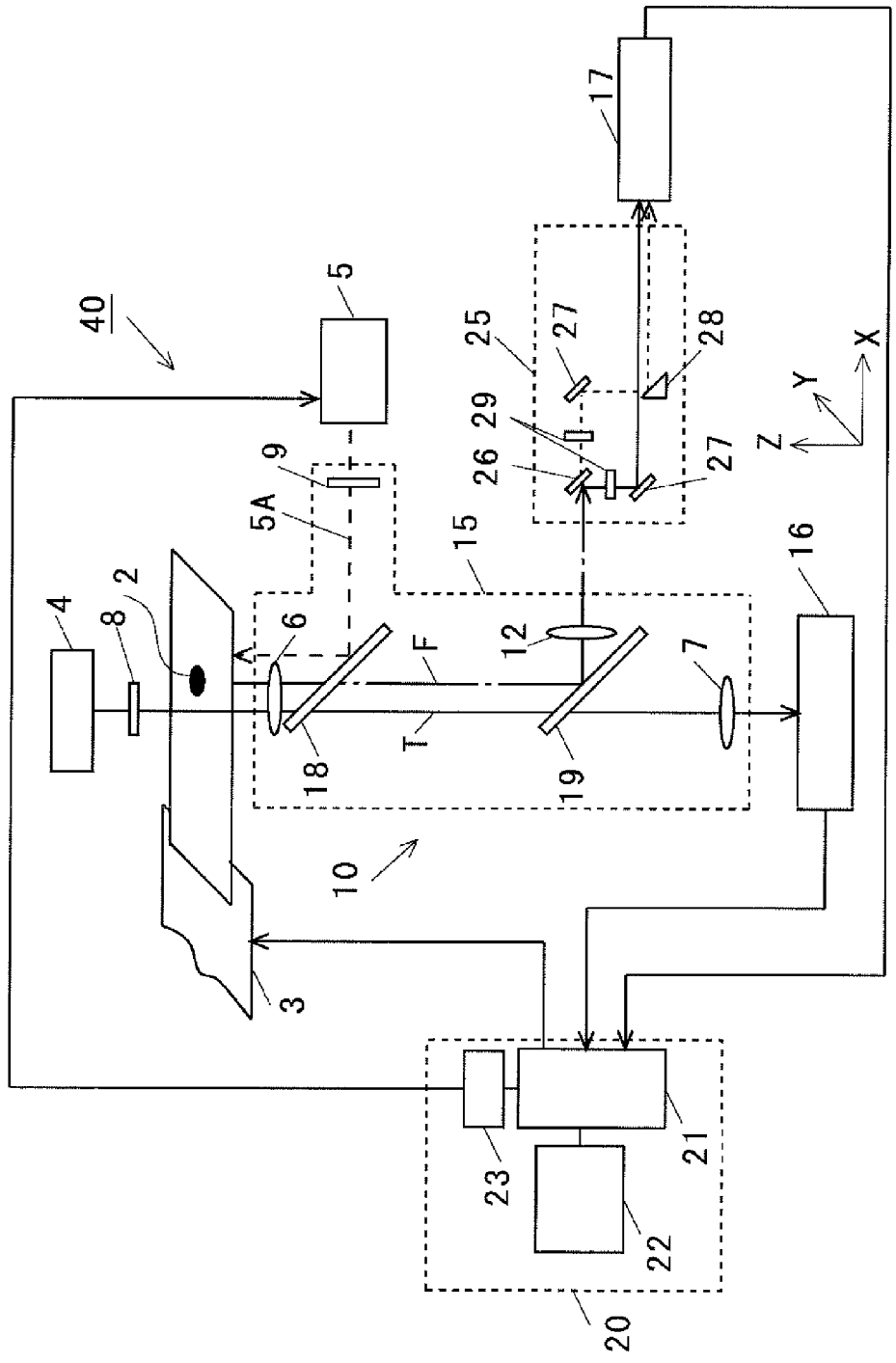
FIG. 6 illustrates a diagram showing the configuration of the microscope in accordance with the Embodiment 4.

FIG. 6 illustrates a diagram showing the configuration of the microscope 40 in accordance with the Embodiment 4 of the present invention.

The configuration of the microscope 40 is the same as that of the microscope 1 except that a fluorescent light wavelength selecting part 25 is installed before the fluorescent image information detecting part 17. The fluorescent light wavelength selecting part 25 is configured to detect two fluorescent wavelengths separately. The fluorescent light wavelength selecting part 25 comprises: a third dichroic mirror 26; a mirror 27; and a prism 28. Furthermore, a lens 29 may be provided. This configuration allows fluorescent light F of two different wavelengths to be detected separately. The fluorescent light wavelength selecting part 25 may be installed in the optical column part 15 or the fluorescent image information detecting part 17. Description of the rest of the configuration will be omitted because it is the same as that of the microscope 1.

The fluorescent light wavelength selecting part 25 exhibits the embodiment for separating fluorescent light F of two different wavelengths. However, fluorescent light F of two or more wavelengths may be detected by using a spectrometer. Namely, the fluorescent light wavelength selecting part 25 may be provided with wavelength selecting means comprised of parts for separating fluorescent light F of one or more wavelengths such as prism and spectrometer.

According to the microscope 40, the type and intensity of excitation light 5A may be controlled. Specifically, the observation time etc. for each of two or more fluorescent dyes s can be determined automatically. It is generally known that some ions and molecules within the cell 2 which are activated or non-activated by their dynamic state or by external stimuli are different. Thus, the wavelength and intensity of the excitation light 5A for exciting the object under observation 2 can be selected according to the moving information of the object under observation 2 and shape of cell, which are obtained by the transmission light images, and accompanying with the kind of stimuli and intensity of stimuli. The fluorescent information from the object under observation 2 can thus be obtained efficiently in conjunction with the information of the object under observation 2 obtained from the transmission light images.

When observing two or more types of cells 2 simultaneously, the type of the cells 2 can be automatically judged through image processing using the area, shape, color concentration, color tone, texture, etc. of each cell 2 (Non-patent Reference 7).

Embodiment 5

Figure 7:
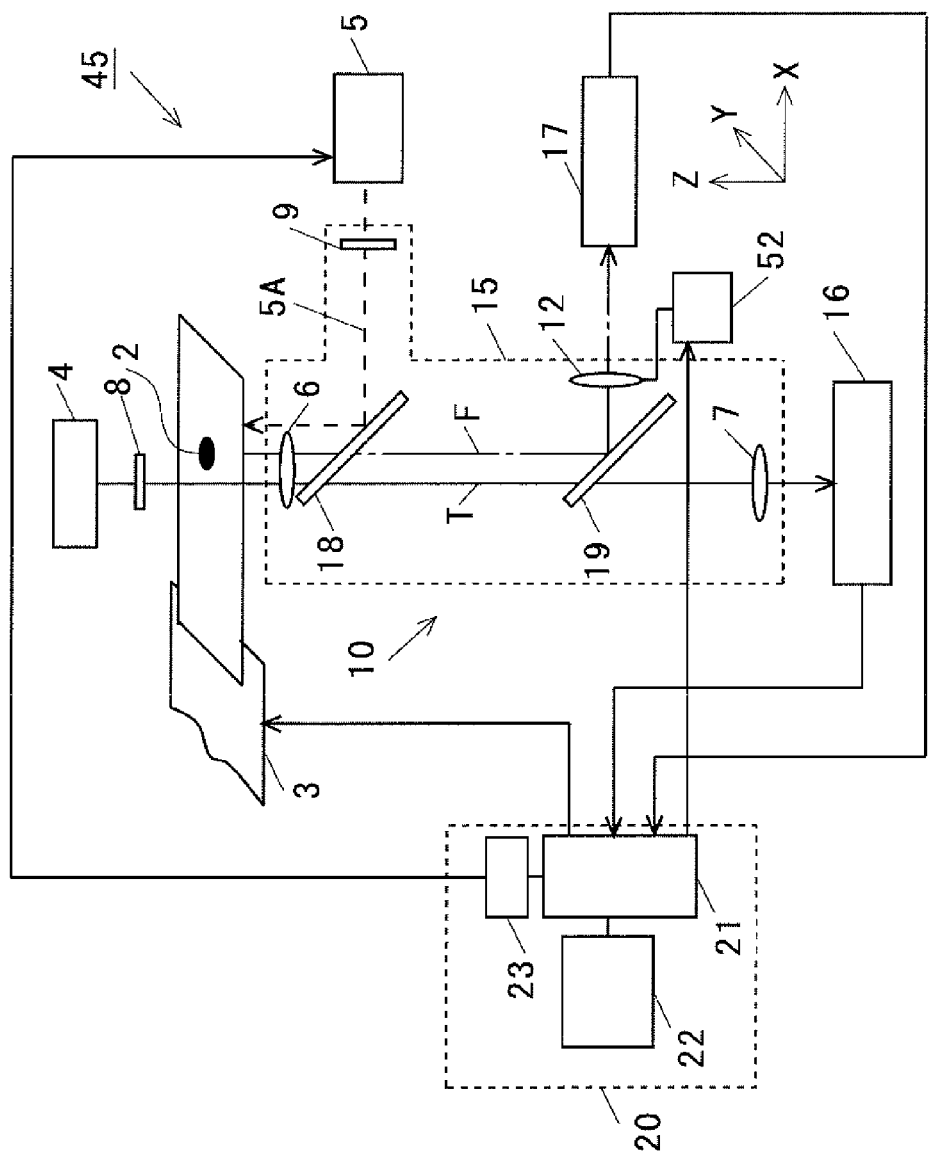
FIG. 7 illustrates a diagram showing the configuration of the microscope in accordance with the Embodiment 5.

FIG. 7 illustrates a diagram showing the configuration of the microscope 45 in accordance with the Embodiment 5 of the present invention.

The configuration of the microscope 45 is the same as that of the microscope 1 except that an imaging lens drive part 52 is installed to allow the imaging lens 12 inserted in the direction of the optical axis of the fluorescent image information detecting part 17 to be transferred in the direction of the optical axis. Description of the rest of the configuration will be omitted because it is the same as that of the microscope 1.

According to the microscope 45, by driving the imaging lens 12 via the imaging lens drive part 52, the position of the focal point of the object under observation 2 can be changed. The imaging lens 12 can be driven independent of the image information detecting part 16 for detecting transmission light, which allows the fluorescent light F from the object under observation 2 to be observed in the direction of the optical axis.

Embodiment 6

Figure 8:
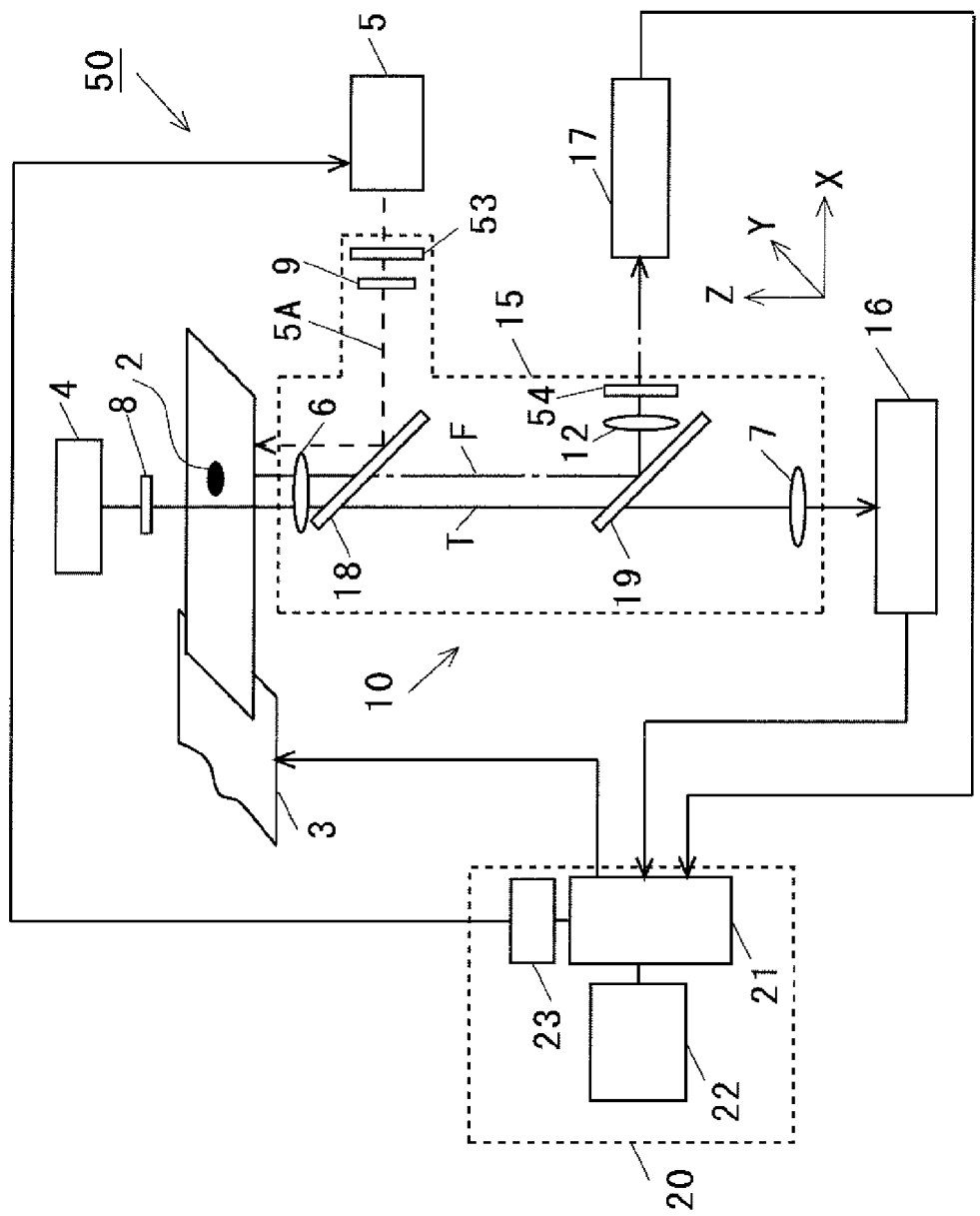
FIG. 8 illustrates a diagram showing the configuration of the microscope in accordance with the Embodiment 6.

FIG. 8 illustrates a diagram showing the configuration of the microscope 50 in accordance with the Embodiment 6 of the present invention.

The configuration of the microscope 50 is the same as that of the microscope 1 except that two pinholes 53 and 54 are provided in the optical system 10 to form a confocal optical system. A first pinhole 53 is installed on the optical axis between the excitation light source 5 and the filter 9. The first pinhole 53 and the filter 9 may be installed in reverse order. A second pinhole 54 is installed on the optical axis between the fluorescent image information detecting part 17 and the imaging lens 12. The second pinhole 54 and the imaging lens 12 may be installed in reverse order. Description of the rest of the configuration will be omitted because it is the same as that of the microscope 1.

According to the microscope 50, the optical system for observing fluorescent light F is a confocal optical system. By installing the first pinhole 53, the irradiation position of the excitation light source 5 can be controlled. By installing the second pinhole 54, the light except from focal point is prevented from entering the fluorescent image information detecting part 17. This allows clear fluorescent images to be obtained. Furthermore, if the stage 3, where the object under observation 2 is placed, is controlled on the XY stage, the object under observation 2 is scanned in response to the transfer of the XY stage 3.

Embodiment 7

Figure 9:
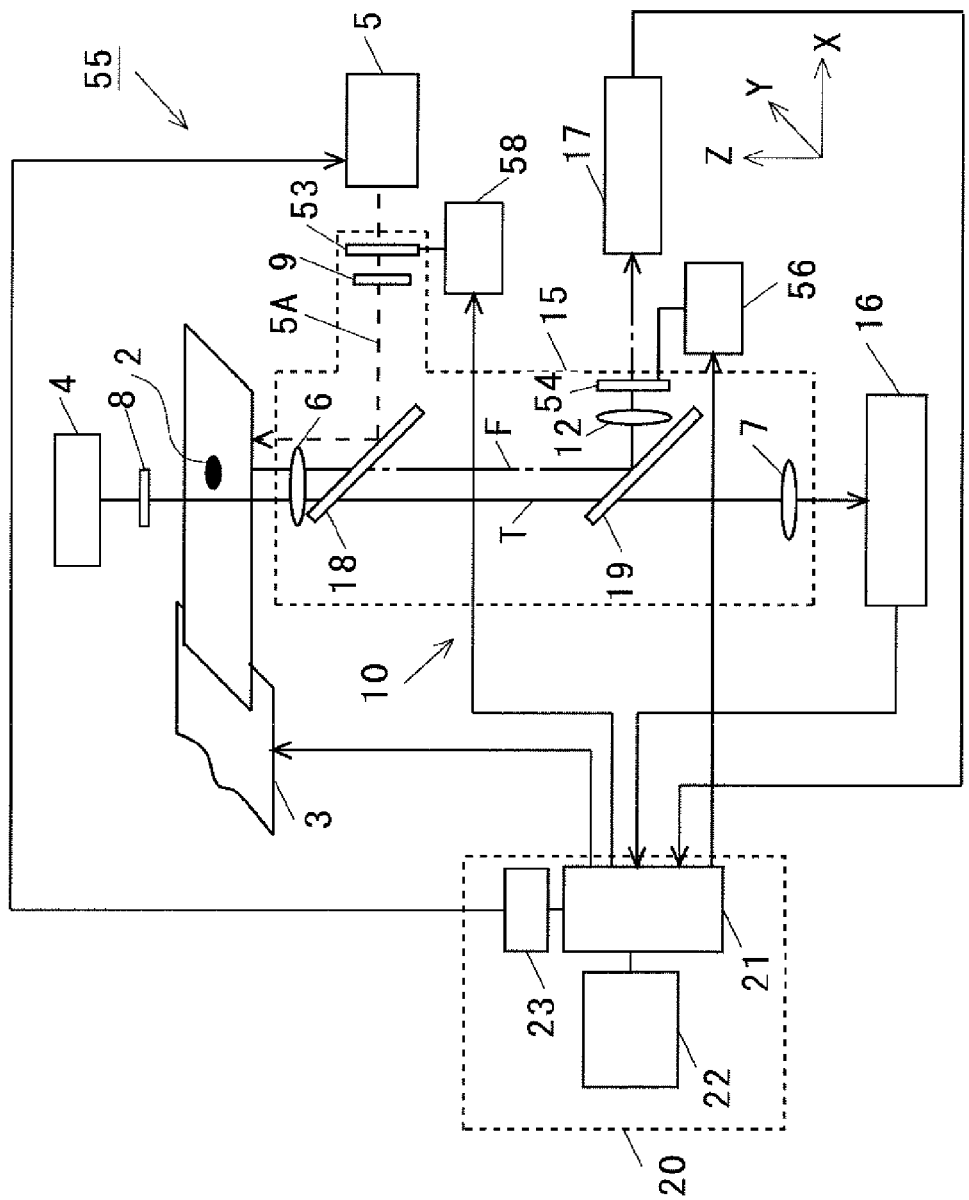
FIG. 9 illustrates a diagram showing the configuration of the microscope in accordance with the Embodiment 7.

FIG. 9 illustrates a diagram showing the configuration of the microscope 55 in accordance with the Embodiment 7 of the present invention.

The configuration of the microscope 55 is the same as that of the microscope 50 except that a pinhole drive part 56 is provided to drive the second pinhole 54 so that the second pinhole 54 is transferred and/or rotated in the direction of the optical axis of the fluorescent light F. Description of the rest of the configuration will be omitted because it is the same as that of the microscope 1.

According to the microscope 55, by driving the second pinhole 54 inserted in the direction of the optical axis of the fluorescent light via the pinhole drive part 56, the focal point of the fluorescent light F from the object under observation 2 and the observation position can be changed. The second pinhole 54 can be driven independent of the image information detecting part 16 for detecting transmission light T. The second pinhole 54 may be configured with two or more holes.

Furthermore, a pinhole drive part 58 for driving the first pinhole 53 may be provided. The irradiation position of the excitation light source 5 can be controlled by transferring and/or rotating the first pinhole 53 along the optical axis. The first pinhole 53 may be configured with two or more holes.

Embodiment 8

Figure 10:
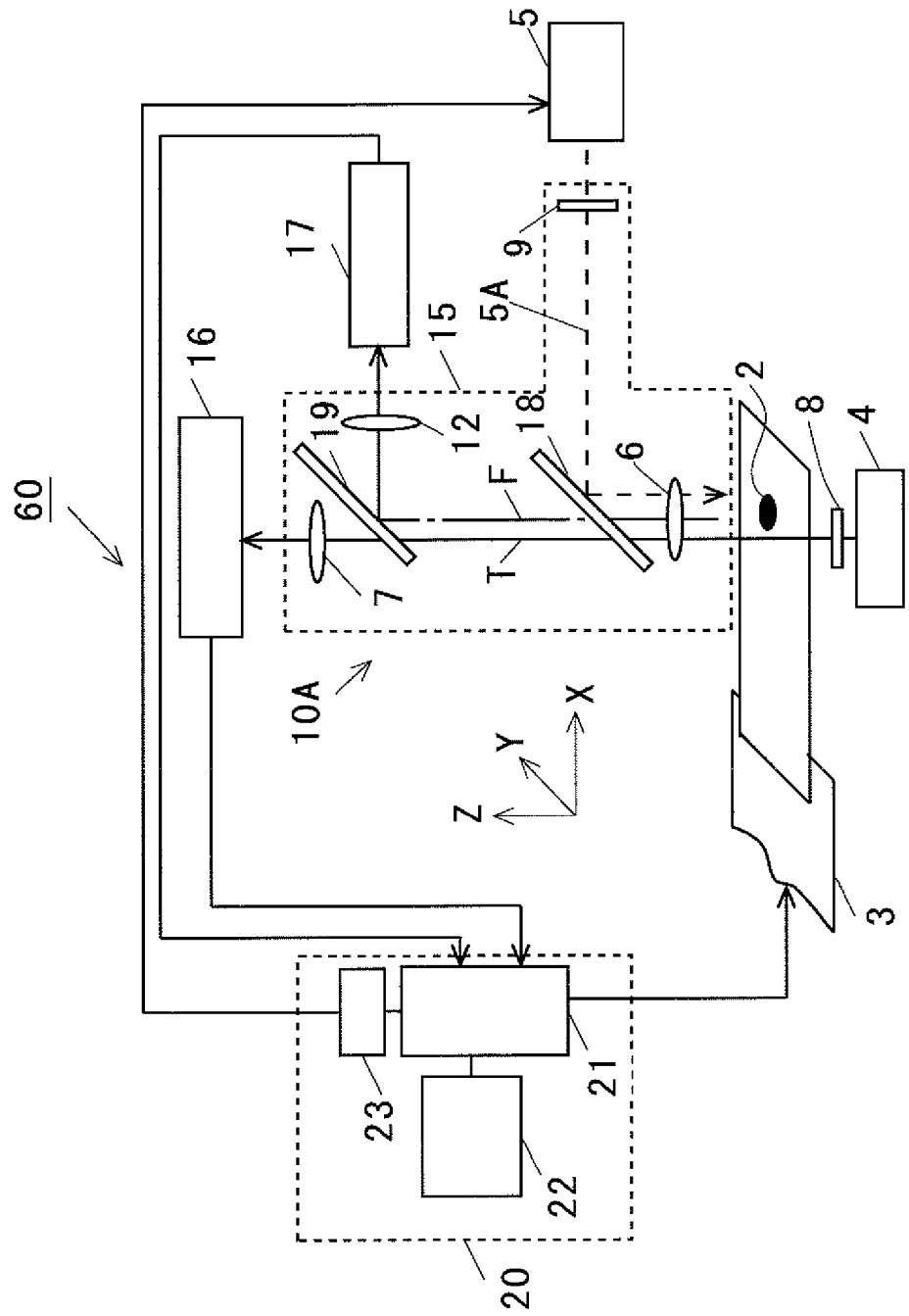
FIG. 10 illustrates a diagram showing the configuration of the microscope in accordance with the Embodiment 8.

FIG. 10 illustrates a diagram showing the configuration of the microscope 60 in accordance with the Embodiment 8 of the present invention.

The configuration of the microscope 60 is the same as that of the microscope 1 except that a so-called upright optical system 10A is provided. In the upright optical system 10A, the transmission light T is irradiated from under the object under observation 2. Description of the rest of the configuration will be omitted because it is the same as that of the microscope 1.

The optical system 10A of the microscope 60 may be configured with the optical system of either one of the microscopes 30, 35, 40, 45, and 55 related to the second to the seventh forms of implementation, or any combinations of these. For example, with the microscope 60, an objective lens drive part 32 may be installed to move the objective lens 6 in the direction of the optical axis (direction of Z-axis) as in the case of the microscope 30.

Furthermore, with the microscope 60, an imaging lens drive part 37 may be installed to move the imaging lens 7 on the side of the image information detecting part 16 in the direction of the optical axis (direction of Z-axis) as in the case of the microscope 35.

In any one of the microscopes 30, 35, 40, 45, 50, 55, and 60, transmission light images and fluorescent images can be observed as same as in the case of the microscope 1.

(Environmental Control of the Object Under Observation)

The environmental control of the object under observation 2 will hereinafter be explained.

Figure 11:
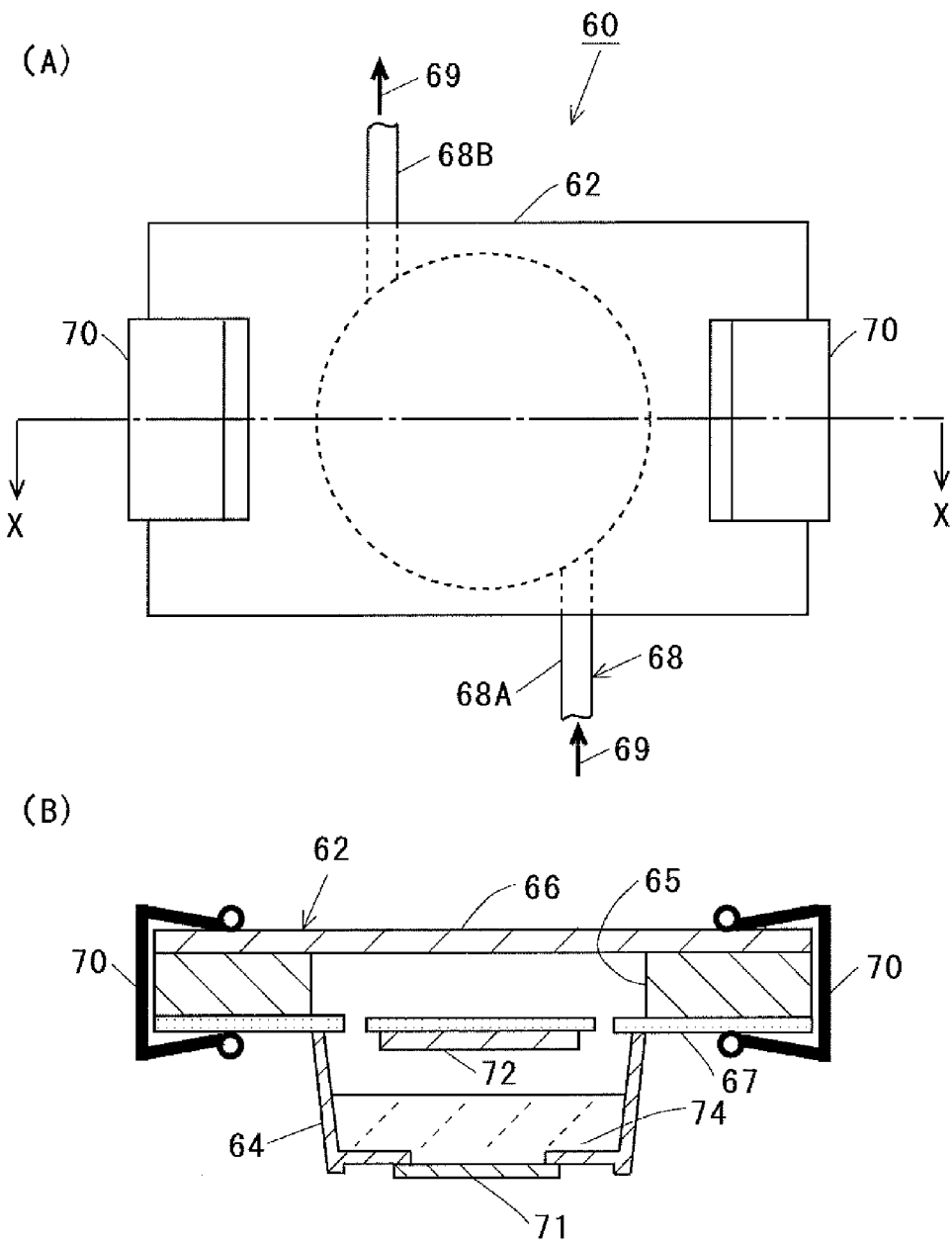
FIG. 11 illustrates a diagram showing the configuration of the environmental control part, in which (A) is a plan view, and (B) is a cross-sectional view taken along the line X-X of (A)

FIG. 11 illustrates a diagram showing the configuration of the environmental control part 60, in which (A) is a plan view, and (B) is a cross-sectional view taken along the line X-X of (A). The environmental control part 60 is configured, including: a main part 62; and a housing part 64 provided under the main part 62 for housing the object under observation 2.

The main part 62 is configured with a resin board 65 sandwiched between a slide glass 66 and a resin film 67. Specifically, the main part 62 comprises: a rectangular resin board 65 having an opening 65A corresponding to the housing part 64; a slide glass 66 which is placed on the resin board 65 to cover the resin board 65; and a resin film 67 which is placed under the resin board 65 to cover the resin board 65. Furthermore, the main part 62 is provided with a gas pipe 68 connected to the opening 65A of the resin board 65. An ambient gas 69 is introduced from the input side 68A to the output side 68B of the gas pipe 68. As ambient gas 69, nitrogen gas, oxygen gas, carbon dioxide, air and any mixture of those gases etc. can be used.

Acrylic resin can be used as the resin board 65 for example. As a resin film 67, a film made of Mylar may be used. Furthermore, a retaining means 70 for retaining the resin board 65, slide glass 66, and resin film 67 may be provided.

The housing part 64 is a container having a dish structure whose uppermost portion is attached to the resin film 67. A cover glass 71 is attached to the bottom of the housing part 64 to seal the opening of the housing part 64. Another cover glass 72 is attached to the bottom of the resin film 67 that faces opposite to the housing part 64. The ambient gas 69 is introduced to the housing part 64 via fine holes 67A made on the resin film 67. The housing part 64 is filled with a culture solution 74 containing the object under observation 2 (not shown). Thus, the object under observation 2 and the culture solution 74 placed in the housing part 64 are exposed to the ambient gas 69.

The object under observation 2 can be observed in a state immersed in the culture solution 74 by mounting the environmental control part 60 on the stage 3 of the microscope 1. Furthermore, if the microscope 1 is housed in a temperature controlled box, the temperature of the culture solution 74 can be maintained at a constant level. Consequently, the transmission light T and fluorescent light F from the object under observation 2 can be observed in a state immersed in the culture solution 74 and the temperature and the ambient gas 69 are maintained at a constant state.

The environmental control part 60 may be constructed to observe two or more objects 2. Specifically, two or more environmental control part s 60 as shown in FIG. 11 may be installed.

Figure 12:
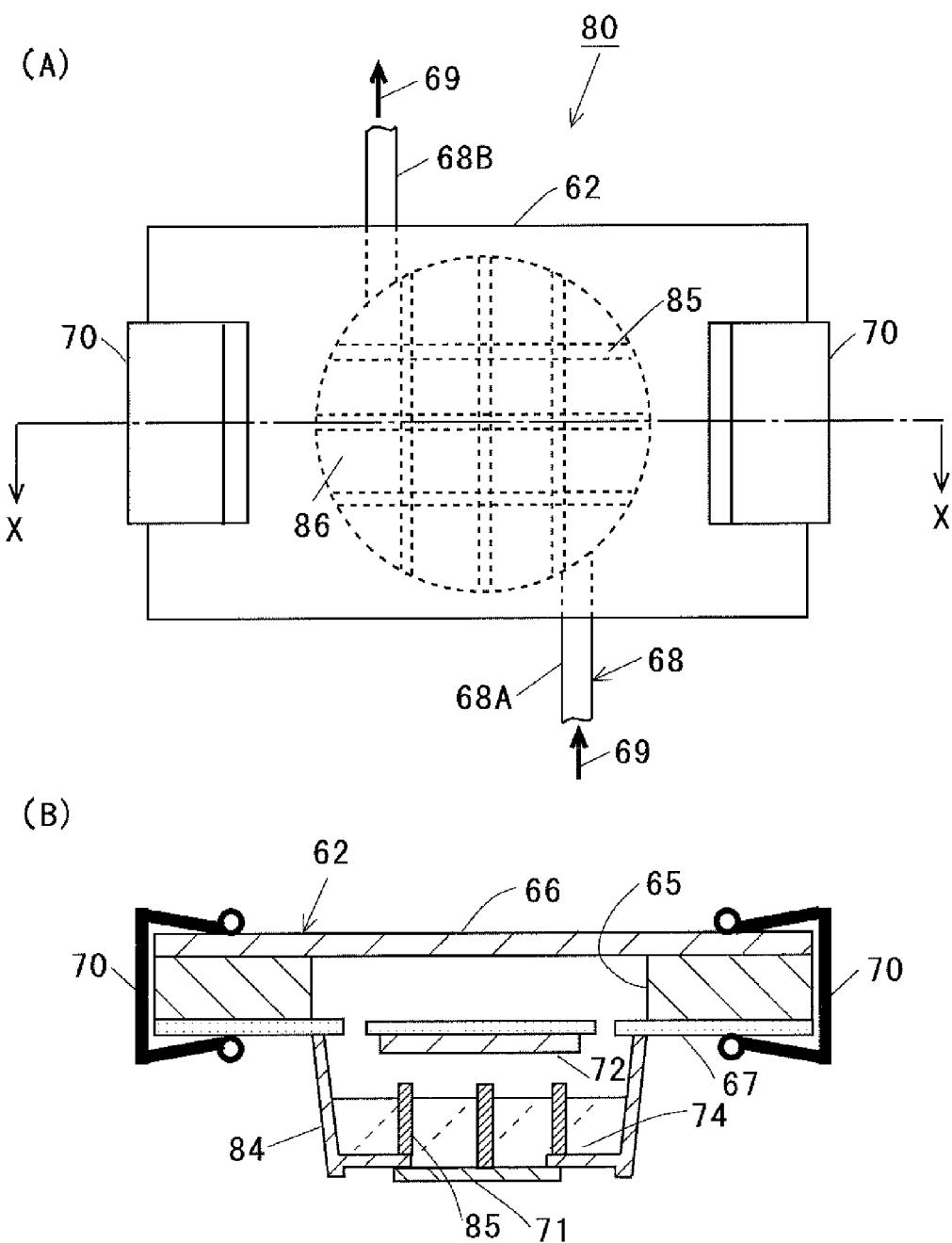
FIG. 12 illustrates a diagram showing another configuration of the environmental control part capable of observing two or more objects, in which (A) is a plan view, and (B) is a cross-sectional view along the line X-X of (A)

FIG. 12 illustrates a diagram showing another configuration of the environmental control part 80 capable of observing two or more i.e. a plural objects, in which (A) is a plan view, and (B) is a cross-sectional view along the line X-X of (A).

The configuration of the environmental control part 80 is the same as that of the environmental control unit 60 except that its housing unit 84 is not of a single space structure but is divided into housing compartments 86 with lattice-shaped walls 85. Each housing compartments 86 is filled with a culture solution 74. Description of the rest of the configuration will be omitted because it is the same as that of the environmental control unit 60.

According to the environmental control unit 80, since the object under observation 2 can be housed in each of the housing compartments 86, transmission light T and fluorescent light F from the objects under observation 2 can be observed with the temperature and the ambient gas 69 maintained in a constant state. Culture solutions 74 of different types may be injected to each of the housing compartments 86, and the cells 2 of the same type can be observed. In this case, the transmission light T and fluorescent light F from each cell 2 resulting from varied culture solution conditions can be observed continuously by the temperature and the ambient gas 69 maintained in a constant state. On the other hand, culture solution 74 of the same type can be injected into each of the housing compartments 86, and different types of cells 2 may be observed.

Furthermore, with the fluorescent observation conducted using the microscope 1 equipped with an environmental control part 60 or 80, the fluorescent information from the object under observation 2 can be obtained efficiently in response to the information of the object under observation 2 obtained from transmission light images. Thus, the irradiation time of the excitation light 5A for generating fluorescent light F to the object under observation 2 can be made shorter. Therefore, when the object under observation 2 is a biological sample such as cells, transmission light T and fluorescent light F can be observed for a longer period compared with the conventional fluorescent observation.

In addition, the environmental control parts 60 and 80 may be equipped with means to stimulate the object under observation 2. Such stimulating means include electrical, magnetic, dynamic, ultrasonic, thermal, chemical, and optical stimuli etc.

Example

The present invention will hereinafter be described in more detail by referring to Example.

A microscope 30 as shown in FIG. 4 was constructed. As the optical system 10, an inverted microscope (made by OLYMPUS, model IX71) was used, and a halogen lamp and a xenon lamp were used as the illumination and excitation light sources 4 and 5 respectively. An objective lens (made by OLYMPUS, model, UApo40x3/340) 6 of 40 magnifications was used.

The camera (made by POINTGREY, model Dragofly Express) was used for the image information detecting part 16 for importing bright field observation images into the personal computer 21. This camera was capable of obtaining 8-bit grayscale images at 100 fps (frame/second). The pixel size is 640×480.

A piezoelectric stage (made by Physik Instrument, model P-723) was used as the objective lens drive part 32 for controlling the position of the objective lens 6 in the direction of the optical axis of the microscope 30. The maximum operating distance of this piezoelectric stage 32 was 350 μm. The piezoelectric stage 32 was moved via voltage application. The D/A conversion board (made by Interface, D/A board, model PCI-3346A) was used to apply voltage to the piezoelectric stage 32.

The personal computer 21 installed with the RT-Linux as the real time OS software was used for the control part 20.

The cooled CCD camera (made by Q-Imaging, model Retiga 2000R, 1600×1200 pixels) was used as the detector in the fluorescent image information detecting part 17. The cooling temperature was set at the level 25° C. lower than the room temperature. The fluorescent light F was isolated from the transmission light T using a dichroic mirror 19 (made by Semrock, model FF01-520/35-25) installed within the dual port of the optical system 10. A filter was selected that each wavelength band are different in order to prevent the excitation light 5A of the fluorescent light F, fluorescent light F, and transmission light T for tracking from interfering with each other. Binning was processed to the cooled CCD camera to put together 4×4 pixels, and 400×300 pixels were obtained. The exposure time was set to 33 ms.

As described previously, a T cell 2, which is a type of immune system cells, was observed following the flow chart as shown in FIG. 3. The interval d was set at 1.5 μm. The width of the fluorescent observation area x(0) was determined depending on the number of cells to be observed. Fluorescent observation and bright field observation were performed simultaneously within the fluorescent observation area at the interval of 1.5 μm. After a standby time of 20 seconds, the fluorescent observation area was determined according to the optimum control law, and the center of the fluorescent observation area was found according to the dynamic model of the cell 2. This procedure, namely performing fluorescent observation and bright field observation simultaneously within the fluorescent observation area at the interval of 1.5 μm, was repeated 60 times (T=60).

Figure 13:
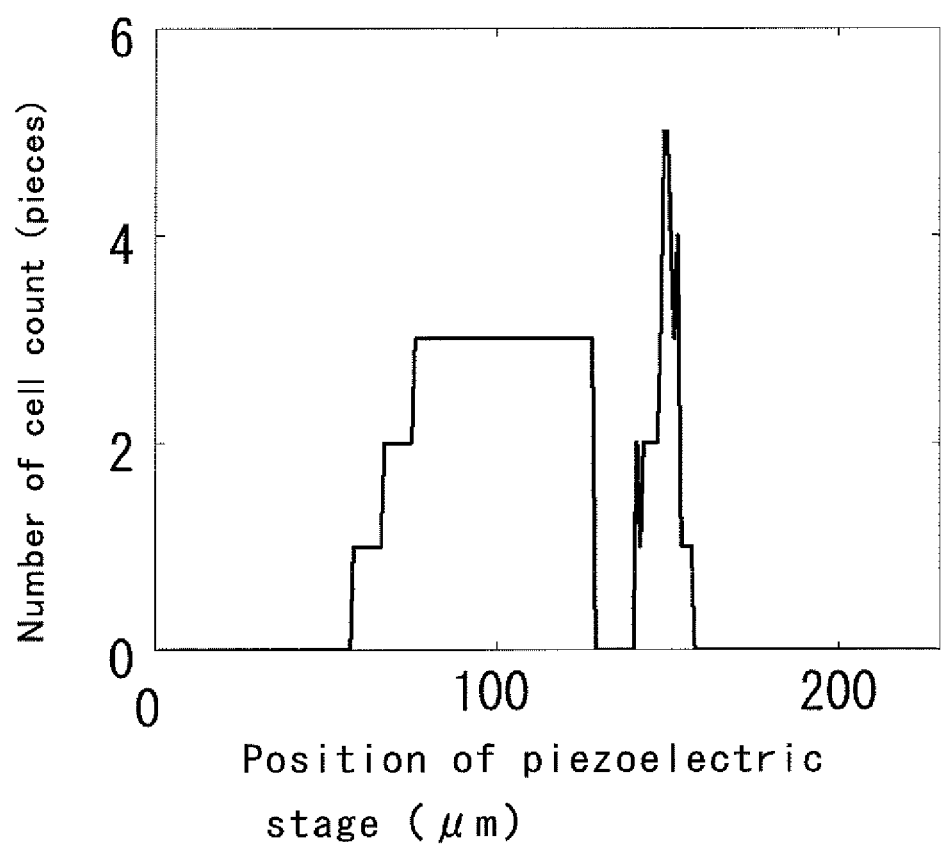
FIG. 13 illustrates an example of cellular distribution immediately after the start of the observation.

FIG. 13 illustrates an example of cellular distribution obtained immediately after the observation was started. The horizontal axis in FIG. 13 represents the position of the piezoelectric stage 32 (μm), and the vertical axis represents the numbers of cell count (pieces).

Figure 14:
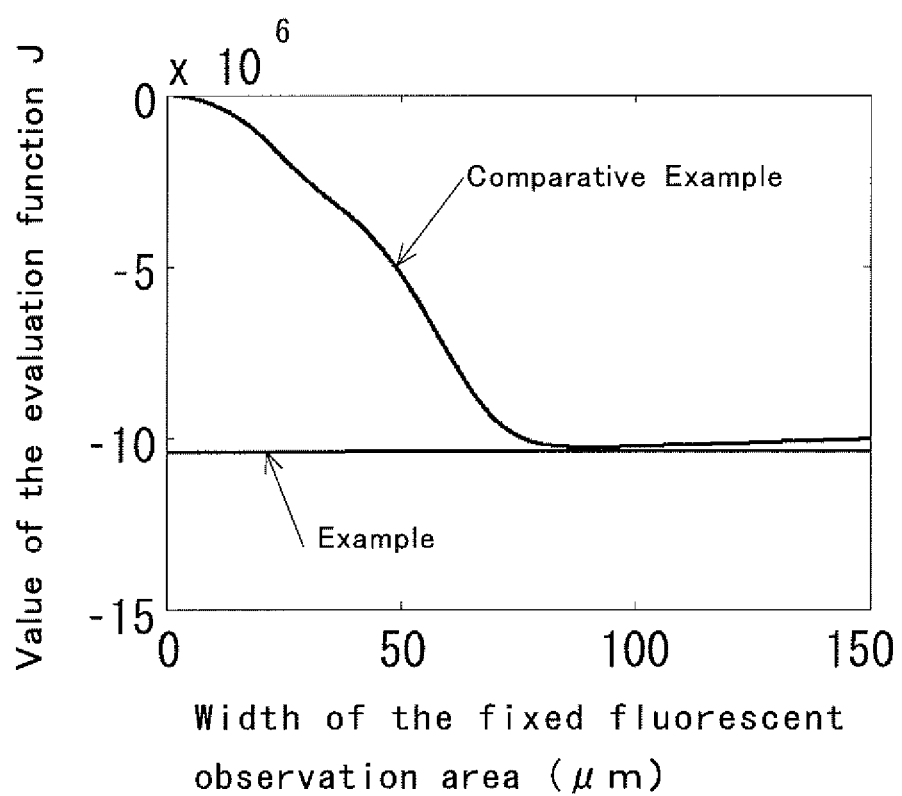
FIG. 14 is a chart comparing the evaluation function J of a form of implementation using a controlled variable U(k) and the evaluation function J of a comparative example, in which the width of the fluorescent observation area is fixed.

FIG. 14 is a chart comparing the evaluation function J of Example using control volume U(k) and that of a Comparative Example in which the width of the fluorescent observation area is fixed. The horizontal axis in FIG. 14 represents the width (μm) of the fluorescent observation area fixed, and the vertical axis represents the value of the evaluation function J. The width of the fluorescent area was changed dynamically using the controlled variable of the present invention.

FIG. 14 indicates the comparison between the evaluation function J in the Example using the controlled variable U(k) and that of the Comparative Example in which the width of the fluorescent observation area is fixed. It is obvious that the value of the evaluation function J in the Example using the controlled variable of the present invention is always smaller than that of the Comparative Example. This means that the optimization of Example was successfully achieved.

Without being limited to the forms of implementation described above, various modifications are allowed with the present invention without departing from the scope described in the claims. It goes without saying that these modifications are included in the scope of the present invention. In the forms of embodiments described above, image sensors were used for the first and the second detecting optical parts 16 and 17. However, to allow visual observation and photo taking at the position of the image sensor, two or more detecting optical system may be used as required. In addition, it is obvious that optimum design and components can be selected to configure the detecting optical part 17 for detecting fluorescent light F depending on the type of the object under observation 2.

The center of the fluorescent observation area can also be found based on the image information of the object under observation, or on the relevant image information and the dynamic model of the object under observation.

The stage may be controlled based on the dynamic model of the object under observation, or on the relevant dynamic model and the above image information.

By adjusting the magnification of the imaging lenses 7 and 12, by reducing the magnification for example, the size of the object under observation in the image obtained by the image information detecting part 16 and the fluorescent image information detecting part 17 can be decreased, and the field of view of observation enlarged, thus allowing simultaneous observation of a larger number of objects. The number of pixels exhibiting the object under observation also decreases, thus further shortening the time required for image processing per cell performed by the control part 20.

DESCRIPTION OF CODES

1, 30, 35, 50, 45, 50, 55, and 60: Microscope
2: Object under observation
3: XY or XYZ stage
4: Illumination light source
5: Excitation light source
5A: Excitation light
6: Objective lens
7: Imaging lens (for transmission light)
8, 9: Filter
10, 10A: Optical system
12: Imaging lens (for fluorescent light)
15: Optical column part
16: Image information detecting part
17: Fluorescent image information detecting part
18, 19: First and second beam splitters (Dichroic mirrors)
20: Control part
21: Personal computer
22: Display
23: Excitation light source control part
25: Fluorescent wavelength selecting part
26: Third dichroic mirror
27: Mirror
28: Prism
29: Lens
32: Objective lens drive part
37: Transmission light imaging lens drive part
52: Fluorescent light imaging lens drive part
53: First pinhole
54: Second pinhole
56, 58: Pinhole drive part
60, 80: Environmental control part
62: Main part
64, 84: Housing part
65: Resin board
66: Slide glass
67: Resin film
67A: Fine hole
68: Gas pipe
68A: Input side
68B: Output side
69: Ambient gas
70: Retaining means
71, 72: Cover glass
74: Culture solution
85: Wall
86: Housing compartments
F: Fluorescent light
T: Transmission light

What is claimed is:

1. A microscope for analyzing a biological tissue, comprising:
   a stage for placing an object under observation that is the biological tissue;
   a first light source with an optical system for radiating illumination light to the object under observation;
   a second light source with an optical system for radiating excitation light for exciting fluorescent light to the object under observation;
   an image detecting part for detecting an image of the object under observation formed by the illumination light;
   a fluorescent image detecting part for detecting a fluorescent image of the biological tissue formed by the fluorescent light, said stage, the fluorescent image detection part, and the second light source being configured to capture a fluorescent image of a horizontal cross section of the biological tissue and a vicinity thereof at multiple levels along a height of the biological tissue; and
   a control part that determines a fluorescent observation portion of the biological tissue from which said fluorescent image of said horizontal cross section is taken at the multiple vertical levels,
   wherein the control part determines the fluorescent observation portion by:
      determining a center of the fluorescent observation portion along a vertical direction using at least either one of the image of the biological tissue detected by the image detecting part or a dynamic model of the biological tissue; and
      determining a vertical length of the fluorescent observation portion by a classic control law that is PID control law or by modern control law that is any one of optimum control law and sub-optimum control law applied to the image detected by the image detecting part,
   wherein, after determining the fluorescent observation portion, the control part causes the image detecting part and the fluorescent image detecting part to detect an image of the biological tissue and a fluorescent image of a horizontal cross section of the biological tissue at multiple levels in the vertical direction within the fluorescent observation portion, said multiple levels being distributed in the vertical length of the fluorescent observation portion at a predetermined interval.

2. The microscope as set forth in claim 1, wherein the control part controls the stage to allow tracking of the object under observation based on at least one of the dynamic model of the object under observation and the image of the object under observation, and also controls collection of the fluorescent image of the object under observation.

3. The microscope as set forth in claim 1, wherein the control part controls the stage by any one of a proportional control method, an integral control method, and a derivative control method, or a classic control that is PID control by combining two or more of said control methods.

4. The microscope as set forth in claim 1, wherein the control part is provided with a first light source control part for controlling the first light source and a second light source control part for controlling the second light source.

5. The microscope as set forth in claim 1, wherein the stage is a two-dimensional or three-dimensional stage for moving the position of the object under observation.

6. The microscope as set forth in claim 1, wherein the fluorescent image detecting part has wavelength selecting means for isolating fluorescent light of one or more wavelengths.

7. The microscope as set forth in claim 1, wherein a first pinhole is provided between the second light source and the object under observation, and a second pinhole is provided between the fluorescent light and the fluorescent image detecting part.

8. The microscope as set forth in claim 7, wherein a pinhole drive part is provided for moving and/or rotating the first pinhole or the second pinhole.

9. The microscope as set forth in claim 1, wherein an objective lens is provided between the first light source and the object under observation, and an objective lens drive part is provided for driving the objective lens.

10. The microscope as set forth in claim 1, wherein an imaging lens is provided between a light generated at the object under observation and the image detecting part, and an imaging lens drive part is provided for driving the imaging lens.

11. The microscope as set forth in claim 1, wherein an imaging lens is provided between the fluorescent light and the fluorescent image detecting part, and an imaging lens drive part is provided for driving the imaging lens.

12. The microscope as set forth in claim 11, wherein an environmental control part is provided, and the environmental control part, which houses the object under observation, is filled with an ambient gas.

13. The microscope as set forth in claim 12, wherein the environmental control part has a housing part capable of housing a plurality of the objects under observation.

14. The microscope as set forth in claim 1, further comprising means for stimulating the object under observation.

15. A fluorescent observation method for a biological tissue for microscopic fluorescent observation, the method comprising:
   a first step of determining a fluorescent observation portion of the object under observation that is the biological tissue, the first step including:
      determining a center of the fluorescent observation portion along a vertical direction using at least either one of a detected image of the biological tissue formed by illumination light or a dynamic model of the biological tissue; and
      determining a vertical length of the fluorescent observation portion by a classic control law that is PID control law or modern control law that is any one of optimum control law and sub-optimum control law applied to the detected image of the biological tissue formed by the illumination light, and
   a second step of obtaining fluorescent images at predetermined positions within the determined fluorescent observation portion, said second step including radiating excitation light for exciting fluorescent light to the biological tissue and obtaining a fluorescent image of a horizontal cross section of the biological tissue at multiple levels in the vertical direction within the fluorescent observation portion, said multiple levels being distributed in the vertical length of the fluorescent observation portion at a predetermined interval.

16. The fluorescent observation method for the object under observation as set forth in claim 15, characterized in that wherein the second step includes obtaining an image of the object under observation formed by the illumination light.

17. The fluorescent observation method as set forth in claim 15 or 16, wherein the first and second steps are repeated after a prescribed time has passed since previous performance of the first and second steps.

18. The fluorescent observation method for object under observation as set forth in claim 15, wherein parameters for the dynamic model include either one of the position, speed, distribution, type, shape, ionic concentration, and molecular concentration of the object under observation, or any combinations of these.

* * * * *